(12) United States Patent
Rosenberg

(10) Patent No.: US 6,323,837 B1
(45) Date of Patent: *Nov. 27, 2001

(54) METHOD AND APPARATUS FOR INTERFACING AN ELONGATED OBJECT WITH A COMPUTER SYSTEM

(75) Inventor: Louis B. Rosenberg, Mountain View, CA (US)

(73) Assignee: Immersion Corporation, San Jose, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/276,012

(22) Filed: Mar. 25, 1999

Related U.S. Application Data

(63) Continuation of application No. 08/833,502, filed on Apr. 7, 1997, now Pat. No. 6,037,927, which is a continuation of application No. 08/275,120, filed on Jul. 14, 1994, now Pat. No. 5,623,582.

(51) Int. Cl.[7] ............................................ G09G 5/00
(52) U.S. Cl. ................................ 345/156; 345/161
(58) Field of Search ......................... 345/7, 8, 161, 345/166, 157, 156, 158, 184; 318/567, 628; 74/471

(56) References Cited

U.S. PATENT DOCUMENTS

| 2,906,179 | 9/1959 | Bower . |
| 3,531,868 | 10/1970 | Stevenson . |
| 3,775,865 | 12/1973 | Rowan . |

(List continued on next page.)

FOREIGN PATENT DOCUMENTS

| 0571827A1 | 12/1993 | (EP) . |
| 2254911A | 10/1992 | (GB) . |

(List continued on next page.)

OTHER PUBLICATIONS

Jacobsen, S.C. et al., "High Performance, High Dexterity, Force Reflective Teleoperator II," ANS Topical Meeting on Robotics & Remote Systems, Albuquerque, New Mexico Feb. 24–27, 1991, pp. 1–10.

(List continued on next page.)

Primary Examiner—Regina Liang
(74) Attorney, Agent, or Firm—Guy V. Tucker; James R. Riegel

(57) ABSTRACT

An apparatus for interfacing the movement of a shaft with a computer includes a support, a gimbal mechanism having two degrees of freedom, and three electromechanical transducers. When a shaft is engaged with the gimbal mechanism, it can move with three degrees of freedom in a spherical coordinate space, where each degree of freedom is sensed by one of the three transducers. A fourth transducer can be used to sense rotation of the shaft around an axis. The method includes the steps of defining an origin in 3-dimensional space, physically constraining a shaft in the 3-dimensional space such that a portion of the shaft always intersects the origin and such that a portion of the shaft extending beyond the origin defines a radius in a spherical coordinate system, transducing a first electrical signal related to a first angular coordinate of the radius with a first transducer, transducing a second electrical signal related to a second angular coordinate with a second transducer, transducing a third electrical signal related to the length of the radius with a third transducer, and coupling the transducers to a computer.

33 Claims, 11 Drawing Sheets

U.S. PATENT DOCUMENTS

| | | |
|---|---|---|
| 3,890,958 | 6/1975 | Fister et al. . |
| 3,919,691 | 11/1975 | Noll ................. 340/172.5 |
| 3,944,798 | 3/1976 | Eaton . |
| 4,216,467 | 8/1980 | Colston ................. 340/365 |
| 4,227,319 | 10/1980 | Guy et al. ................. 35/12 |
| 4,360,345 | 11/1982 | Hon . |
| 4,391,282 | 7/1983 | Ando et al. ................. 128/660 |
| 4,398,889 | 8/1983 | Lam et al. ................. 434/45 |
| 4,477,043 | 10/1984 | Repperger ................. 244/223 |
| 4,477,973 | 10/1984 | Davies . |
| 4,571,834 | 2/1986 | Fraser et al. . |
| 4,593,470 | 6/1986 | Davies ................. 33/1 CC |
| 4,632,341 | 12/1986 | Repperger et al. ................. 244/230 |
| 4,638,798 | 1/1987 | Shelden et al. . |
| 4,642,055 | 2/1987 | Saliterman . |
| 4,653,011 | 3/1987 | Iwano . |
| 4,654,648 | 3/1987 | Herrington et al. . |
| 4,676,002 | 6/1987 | Slocum . |
| 4,679,331 | 7/1987 | Koontz . |
| 4,680,519 | 7/1987 | Chand et al. . |
| 4,703,443 | 10/1987 | Moriyasu . |
| 4,750,487 | 6/1988 | Zanetti . |
| 4,769,763 | 9/1988 | Trieb et al. . |
| 4,787,051 | 11/1988 | Olson . |
| 4,791,934 | 12/1988 | Brunnett . |
| 4,800,721 | 1/1989 | Cemenska et al. . |
| 4,811,608 | 3/1989 | Hilton ................. 73/862.04 |
| 4,819,195 | 4/1989 | Bell et al. . |
| 4,839,838 | 6/1989 | LaBiche et al. . |
| 4,849,692 | 7/1989 | Blood . |
| 4,868,549 | 9/1989 | Affinito et al. ................. 340/710 |
| 4,879,556 | 11/1989 | Duimel . |
| 4,879,668 | 11/1989 | Cline et al. . |
| 4,888,877 | 12/1989 | Enderle et al. . |
| 4,891,889 | 1/1990 | Tomelleri . |
| 4,896,554 | 1/1990 | Culver ................. 318/561 |
| 4,907,970 | 3/1990 | Meenen, Jr. . |
| 4,907,973 | 3/1990 | Hon . |
| 4,942,545 | 7/1990 | Sapia . |
| 4,945,305 | 7/1990 | Blood . |
| 4,945,501 | 7/1990 | Bell et al. . |
| 4,961,138 | 10/1990 | Gorniak . |
| 4,962,591 | 10/1990 | Zeller et al. . |
| 4,982,504 | 1/1991 | Söderberg et al. . |
| 5,007,085 | 4/1991 | Greanias et al. . |
| 5,007,300 | 4/1991 | Siva ................. 74/471 XY |
| 5,040,306 | 8/1991 | McMurtry et al. . |
| 5,044,956 | 9/1991 | Behensky et al. ................. 434/45 |
| 5,050,608 | 9/1991 | Watanabe et al. . |
| 5,067,072 | 11/1991 | Talati et al. ................. 395/650 |
| 5,072,361 | 12/1991 | Davis et al. ................. 364/167.01 |
| 5,088,046 | 2/1992 | McMurtry et al. . |
| 5,088,055 | 2/1992 | Oyama . |
| 5,095,303 | 3/1992 | Clark et al. . |
| 5,103,404 | 4/1992 | McIntosh ................. 318/568.22 |
| 5,107,080 | 4/1992 | Rosen ................. 200/6 A |
| 5,116,051 | 5/1992 | Moncrief et al. ................. 273/448 B |
| 5,128,671 | 7/1992 | Thomas, Jr. . |
| 5,131,844 | 7/1992 | Marinaccio et al. . |
| 5,132,672 | 7/1992 | Clark . |
| 5,139,261 | 8/1992 | Openiano . |
| 5,142,506 | 8/1992 | Edwards . |
| 5,142,931 | 9/1992 | Menahem ................. 74/471 XY |
| 5,143,505 | 9/1992 | Burdea et al. . |
| 5,146,566 | 9/1992 | Hollis, Jr. et al. ................. 395/275 |
| 5,148,377 | 9/1992 | McDonald . |
| 5,149,270 | 9/1992 | McKeown ................. 434/262 |
| 5,162,713 | 11/1992 | Mohri et al. . |
| 5,181,181 | 1/1993 | Glynn . |
| 5,182,557 | 1/1993 | Lang ................. 341/20 |
| 5,184,319 | 2/1993 | Kramer . |
| 5,185,561 | 2/1993 | Good et al. ................. 318/432 |
| 5,187,874 | 2/1993 | Takahashi et al. . |
| 5,189,806 | 3/1993 | McMurtry et al. . |
| 5,193,963 | 3/1993 | McAffee et al. ................. 414/5 |
| 5,204,824 | 4/1993 | Fujimaki . |
| 5,220,260 | 6/1993 | Schuler ................. 318/561 |
| 5,223,776 | 6/1993 | Radke et al. ................. 318/568.1 |
| 5,228,356 | 7/1993 | Chuang . |
| 5,230,623 | 7/1993 | Guthrie et al. ................. 433/72 |
| 5,251,127 | 10/1993 | Raab . |
| 5,251,156 | 10/1993 | Heier et al. . |
| 5,259,120 | 11/1993 | Chapman et al. . |
| 5,275,565 | 1/1994 | Moncrief ................. 434/29 |
| 5,295,694 | 3/1994 | Levin . |
| 5,296,846 | 3/1994 | Ledley ................. 345/161 |
| 5,317,336 | 5/1994 | Hall ................. 345/164 |
| 5,337,412 | 8/1994 | Baker et al. . |
| 5,351,692 | 10/1994 | Dow et al. . |
| 5,354,162 | 10/1994 | Burdea et al. ................. 414/5 |
| 5,379,663 | 1/1995 | Hara . |
| 5,384,460 | 1/1995 | Tseng . |
| 5,389,865 | 2/1995 | Jacobus et al. ................. 318/568.11 |
| 5,396,266 | 3/1995 | Brimhall ................. 345/161 |
| 5,397,323 | 3/1995 | Taylor . |
| 5,402,582 | 4/1995 | Raab . |
| 5,403,191 | 4/1995 | Tuason . |
| 5,405,152 | 4/1995 | Katanics et al. . |
| 5,414,337 | 5/1995 | Schuler ................. 318/561 |
| 5,417,696 | 5/1995 | Kashuba et al. . |
| 5,428,748 | 6/1995 | Davidson et al. ................. 395/275 |
| 5,429,140 | 7/1995 | Burdea et al. ................. 128/774 |
| 5,436,542 | 7/1995 | Petelin et al. . |
| 5,436,638 | 7/1995 | Bolas et al. ................. 345/156 |
| 5,445,166 | 8/1995 | Taylor . |
| 5,459,382 | 10/1995 | Jacobus et al. ................. 318/568.11 |
| 5,467,763 | 11/1995 | McMahon et al. . |
| 5,482,051 | 1/1996 | Reddy et al. ................. 128/733 |
| 5,512,919 | 4/1996 | Araki ................. 345/156 |
| 5,513,100 | 4/1996 | Parker et al. ................. 364/167.01 |
| 5,576,727 | 11/1996 | Rosenberg et al. ................. 345/179 |
| 5,577,981 | 11/1996 | Jarvik ................. 482/4 |
| 5,587,937 | 12/1996 | Massie et al. . |
| 5,589,828 | 12/1996 | Armstrong ................. 341/20 |
| 5,609,485 | 3/1997 | Bergman et al. . |
| 5,623,582 | * 4/1997 | Rosenbern ................. 345/161 |
| 5,629,594 | 5/1997 | Jacobus et al. . |
| 5,643,087 | 7/1997 | Marcus et al. ................. 463/38 |
| 5,701,140 | 12/1997 | Rosenberg et al. ................. 345/156 |
| 5,704,791 | 1/1998 | Gillio . |
| 5,709,219 | 1/1998 | Chen et al. ................. 128/782 |
| 5,721,566 | 2/1998 | Rosenberg ................. 345/161 |
| 5,731,804 | 3/1998 | Rosenberg ................. 345/156 |
| 5,734,373 | 3/1998 | Rosenberg et al. ................. 345/161 |
| 5,755,577 | 5/1998 | Gillio ................. 434/262 |
| 5,767,839 | 6/1998 | Rosenberg ................. 345/161 |
| 5,769,640 | 6/1998 | Jacobus et al. ................. 434/262 |
| 5,790,108 | 8/1998 | Salcudean et al. ................. 345/184 |
| 5,805,140 | 9/1998 | Rosenberg et al. ................. 345/161 |
| 5,808,665 | 9/1998 | Green ................. 348/65 |
| 5,821,920 | 10/1998 | Rosenberg et al. ................. 345/156 |
| 5,889,672 | 3/1999 | Schuler et al. ................. 364/188 |
| 5,920,319 | 7/1999 | Vining et al. . |
| 5,944,151 | 8/1999 | Jakobs et al. ................. 188/267.1 |
| 6,004,134 | 12/1999 | Marcus et al. ................. 434/45 |
| 6,024,576 | 2/2000 | Bevirt et al. ................. 434/262 |
| 6,037,927 | * 3/2000 | Rosenbern ................. 345/161 |

FOREIGN PATENT DOCUMENTS

| | | |
|---|---|---|
| 434610A | 2/1992 | (JP) . |
| WO91/06935 | 5/1991 | (WO) . |

| | | |
|---|---|---|
| WO9400052 | 1/1994 | (WO) . |
| WO9426167 | 11/1994 | (WO) . |
| WO95/02233 | 1/1995 | (WO) . |
| WO9502801 | 1/1995 | (WO) . |
| WO9520787 | 8/1995 | (WO) . |
| WO9520788 | 8/1995 | (WO) . |
| WO9616397 | 5/1996 | (WO) . |
| WO9622591 | 7/1996 | (WO) . |
| WO9639944 | 12/1996 | (WO) . |

OTHER PUBLICATIONS

Kotoku, Tetsuo et al., "Environment Modeling for the Interactive Display (EMID) Used in Telerobotic Systems," IEEE Nov. 3–5, 1991, pp. 99–1004.

Bejczy, Antal K., "The Phantom Robot: Predictive Displays for Teleoperation with Time Delay," IEEE 1990, pp. 546–550.

Buttolo, Pietro et al., "Pen–Based Force Display for Precision Manipulation in Virtual Environments," IEEE Mar. 1995, pp. 1–8.

Tan, Hong Z. et al., "Human Factors for the Design of Force–Reflecting Haptic Interfaces," Tan, Srinivasan, Eberman, & Chang, ASME WAM 1994, pp. 1–11.

Ellis, R.E. et al., "Design and Evaluation of a High–Performance Prototype Planar Haptic Interface," ASME Dec. 3, 1993, DSC–vol. 49, pp. 55–64.

Adelstein Bernard D. et al., "A High Performance Two Degree–of–Freedom Kinesthetic Interface," Massachusetts Institute of Technology 1992, pp. 108–102.

Colgate J. Edward et al., Implementation of Stiff Virtual Walls in Force–Reflecting Interfaces, Sep. 22, 1993.

Iwata, Hiroo et al., Volume Haptization, IEEE 1993, pp. 16–18.

Adelstein Bernard D. et al., "A High Performance Two Degree–of–Freedom Kinesthetic Interface," Massachusetts Institute of Technology 1992, pp. 108–112.

Colgat J. Edward et al., Implementation of Stiff Virtual Walls in Force–Reflecting Interfaces, Sep. 22, 1993.

Iwata, Hiroo et al, Volume Haptization, IEEE 1993, pp. 16–18.

Fischer, Patrick et al., "Specification and Design of Input Devices for Teleoperation," 1990.

Burdea, Grigore et al., "Distributed Virtual Force Feedback," IEEE, May 2, 1993, pp. 25–44.

Rosenberg, Louis B., "The Use of Virtual Fixtures as Perceptual Overlays to Enhance Operator Performance in Remote Environoments," Air Force Material Command, Sep. 1992, pp. 1–42.

Rosenberg, Louis B., Crew Systems Directorate Biodynamics and Biocommunications Division Wright–Patterson, Air Force Material Command, Mar. 1993, pp. 1–45.

Rosenberg, Louis B., "Perceptual Design of a Virtual Rigid Surface Contact," Center for Design Reseach Stanford University, Air Force Material Command, Apr. 1993, pp. 1–41.

Rosenberg, Louis B. et al., "Perceptual Decomposition of Virtual Haptic Surfaces," IEEE, Oct. 1993.

Rosenberg, Louis B., "Virtual Fixtures as Tools to Enhance Operator Performance in Teleprensece Environments," SPIE Telemanipulator Technology, 1993.

Rosenberg, Louis B., "Virtual Haptic Overlays Enhance Performance in Telepresence Tasks," SPIE 1994.

Burdea, Grigore et al., "Dextrous Telerobotics with Force Feedback–An Overview," Robotica 1991, vol. 9.

Colgate, J. Edward et al., "Implementation of STiff Virtual Walls in Force–Reflecting Interfaces," 1993, pp. 1–9.

Yamakita, M. et al. Tele–Virtual Reality of Dynamic Mechanical Model, IEEE Jul. 7–10, 1992, pp. 1103–1110.

Adlestein, Bernard D. et al., "Design and Implementation of a Force Reflecting Manipulandum for Manual Control Research," 1992, pp. 1–24.

Ouh–young, Ming et al., "Force Display Performs Better than Visual Display in a Simple 6–D Docking Task," IEEE 1989, pp. 1462–1466.

Kim, Won S. et al., "Graphics Displays for Operator Aid in Telemanipulation," IEEE 1991, pp. 1059–1067.

Hannaford, Blake et al., "Performance Evaluation of a Six–Axis Generalized Force–Reflecting Teleoperator," IEEE May/Jun. 1991, vol. 21, No. 3, pp. 620–633.

Kim, Won S. et al., A Teleoperation Training Simulator with Visual and Kinesthetic Force Virtual Reality.

Burdea, Grigore et al., "A Portable Dextrous Master with Force Feedback," Presence: Teleoperators and Virtual Environments, MIT Press, Jun. 1991.

Fisher, S.S. et al., "Virtual Environment Display System," ACM Interactive 3D Graphics, Oct. 1986.

"The Personal Digitizer™," Immersion Human Interface Corporation 1994.

"Immersion Probe–MD™," Immersion Human Interface Corporation.

Smith, Geoffrey, "Call It Palpable Progress," Business Week, Oct. 9, 1995, p. 93, 96.

Meyer, Kenneth et al., "A Survey of Position Trackers," The Massachusetts Institute of Technology 1992, Presence, vol. 1, No. 2.

"3D Immersion Interface Tool," Immersion Probe™, 1993.

"Useful Technology for Your File," Designer's Corner, Design News, Mar. 7, 1994.

Minsky, M. et al., "Feeling and Seeing: Issues in Force Display," Association for Computing Machinery, 1990, pp. 235–270.

Snow, E. et al., "Compact Force–Reflecting Hand Controller," NASA Tech Brief, vol. 15, No. 4, Item 153, Apr. 1991, pp. I, 1–3, 1a–15a.

Bostrom, M. et al., "Design of An Interactive Lumbar Puncture Simulator With Tactile Feedback," IEEE 0–7803–1363–1, 1993, pp. 280–286.

Atkinson, W. et al., "Computing with Feeling," Comput. & Graphics, vol. 2, Pergamon Press, 1977, pp. 97–103.

Winey III, Calvin, "Computer Simulated Visual and Tactile Feedback as an Aid to Manipulator and Vehicle Control," MIT Dept. of Mech. Engineering, 1981, pp. 1–79.

Howe, R. et al., "Task Performance with a Dextrous Teleoperated Hand System," Telemanipulator Technology '92, Proceedings of SPIE, vol. 1833, Nov. 1992, pp. 1–9.

Kotoku, Tetsuo, "A Predictive Display with Force Feedback and its Application to Remote Manipulation System with Transmission Time Delay," Prcoeedings of the 1992 IEEE Int'l Conf. on Intelligent Robots and Systems, 1992, pp. 239–246.

Kotoku, T. et al., "Environment Modeling for the Interactive Display (EMID) used in Telerobotic Systems," IROS '91, IEEE Cat. No. 91TH0375–6, pp. 999–1004.

Batter, J. et al., "Grope–1: A Computer Display to the Sense of Feel," Proc. IFIP Congress 1971, pp. 759–763.

Ouh–young, M., "Force Display in Molecular Docking," Univ. of N. Carolina, 1990, pp. 1–12, 66–85.

Iwata, H., "Artificial Reality with Force Feedback: Development of Desktop Virtual Space with Compact Master Manipulator," Computer Graphics, vol. 24, No. 4, 1990, pp. 165–170.

Tan, H. et al., "Manual Resolution of Compliance when Work and Force Cues are Minimized," DSC–vol. 49, Advances in Robotics, Mechatronics, and Haptic Interfaces, ASME 1993, pp. 99–104.

Schmult, B. et al., "Application Areas for a Force–Feedback Joystick," DSC–vol. 49, Advances in Robotics, Mechatronics, and Haptic Interfaces, ASME 1993, pp. 47–54.

Russo, M., "The Design and Implementation of a Three Degree-of-Freedom Force Output Joystick," Dept. of Mech. Engineering, 1990.

Kilpatrick, P., "The Use of a Kinesthetic Supplement in an Interactive Graphics System," Univ. of North Carolina, Computer Science, 1976, pp. 1–175.

Hirota, Koichi et al., "Development of Surface Display," IEEE 0-7803-1363-1, 1993, pp. 256–262.

Hon, David, "Ixion's Realistic Medical Simulations" Virtual Reality World, Jul./Aug. 1994, pp. 59–62.

Merril, Jonathan, et al., "Cyber Surgery: Cutting Costs, Sewing Benefits" Virtual Reality Special Report, Summer 1994, pp. 39, 40, and 42.

Merril, Jonathan, et al., "Surgical Simulation Using Virtual Reality Technology: Design, Implementation, and Implications" Surgical Technology International III, pp. 53–60.

Merril, Jonathan, et al. "Virtual Reality for Trade Shows and Individual Physician Training" Medical Applications, pp. 40–44, Spring 1994.

Cover, Stephen A., et al., "Interactively Deformable Models for Surgery Simulation" IEEE Computer Graphics & Applications, pp. 68–75, Nov. 1993.

* cited by examiner

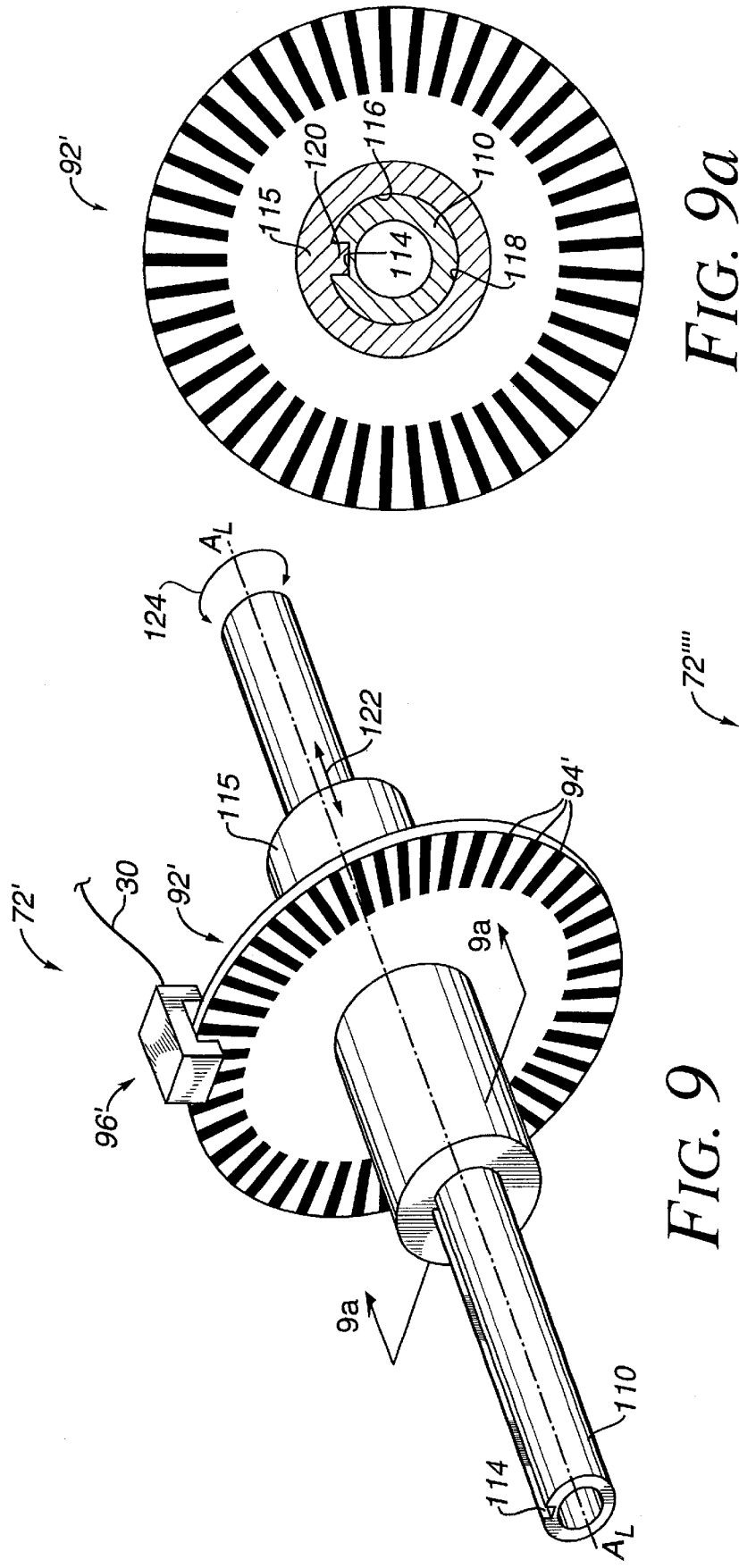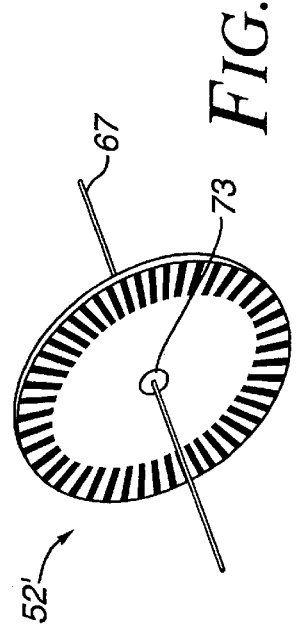

METHOD AND APPARATUS FOR INTERFACING AN ELONGATED OBJECT WITH A COMPUTER SYSTEM

This is a continuation application of prior application Ser. No. 08/833,502, filed on Apr. 7, 1997, now U.S. Pat. No. 6,037,927, which is a continuation of U.S. patent application Ser. No. 08/275,120, filed Jul. 14, 1994, issued as U.S. Pat. No. 5,623,582, all of which are incorporated herein by reference.

BACKGROUND OF THE INVENTION

This invention relates generally to human/computer interface devices, and more particularly to computer input devices such as mice, trackballs, etc.

Virtual reality computer systems provide users with the illusion that they are part of a "virtual" environment. A virtual reality system will typically include a personal computer or workstation, specialized virtual reality software, and virtual reality I/O devices such as head mounted displays, pointer gloves, 3D pointers, etc.

For example, a virtual reality computer system can allow a doctor-trainee or other human operator or user to "manipulate" a scalpel or probe within a computer-simulated "body", and thereby perform medical procedures on a virtual patient. In this instance, the I/O device is typically a 3D pointer, stylus, or the like. As the "scalpel" or "probe" moves within the body image displayed on the screen of the computer system, results of such movement are updated and displayed so that the operator can gain the experience of such a procedure without practicing on an actual human being or a cadaver.

For virtual reality systems to provide a realistic (and therefore effective) experience for the user, sensory feedback and manual interaction should be as natural as possible. As virtual reality systems become more powerful and as the number of potential applications increases, there is a growing need for specific human/computer interface devices which allow users to interface with computer simulations with tools that realistically emulate the activities being represented within the virtual simulation. Such procedures as laparoscopic surgery, catheter insertion, and epidural analgesia should be realistically simulated with suitable human/computer interface devices if the doctor is to be properly trained.

While the state of the art in virtual simulation and medical imaging provides a rich and realistic visual feedback, there is a great need for new human/computer interface tools which allow users to perform natural manual interactions with the computer simulation. For medical simulation, there is a strong need to provide doctors with a realistic mechanism for performing the manual activities associated with medical procedures while allowing a computer to accurately keep track of their actions.

There are number of devices that are commercially available for interfacing a human with a computer for virtual reality simulations. There are, for example, such 2-dimensional input devices such as mice, trackballs, and digitizing tablets. However, 2-dimensional input devices tend to be awkward and inadequate to the task of interfacing with 3-dimensional virtual reality simulations. In contrast, a 3-dimensional human/computer interface tool sold under the trademark Immersion PROBE™ is marketed by Immersion Human Interface Corporation of Palo Alto, Calif., and allows manual control in 3-dimensional virtual reality computer environments. A pen-like stylus allows for dexterous 3-dimensional manipulation, and the position and orientation of the stylus is communicated to a host computer. The Immersion PROBE has six degrees of freedom which convey spatial coordinates (x, y, z) and orientation (role, pitch, yaw) of the stylus to the host computer.

While the Immersion PROBE is an excellent 3-dimensional interface tool, it may be inappropriate for certain virtual reality simulation applications. For example, in some of the aforementioned medical simulations three or four degrees of freedom of a 3-dimensional human/computer interface tool is sufficient and, often, more desirable than five or six degrees of freedom because it more accurately mimics the real-life constraints of the actual medical procedure. Therefore, a less complex, more compact, lighter weight, lower inertia and less expensive alternative to six degree of freedom human/computer interface tool is desirable for certain applications.

SUMMARY OF THE INVENTION

The present invention provides a 3-dimensional human/computer interface tool which is particularly well adapted to virtual reality simulation systems that require fewer degrees of freedom, e.g. two, three, or four degrees of freedom. The present invention therefore tends to be less complex, more compact, lighter weight, less expensive, more reliable and have less inertia than 3-dimensional human/computer interface tools of the prior art having more degrees of freedom.

The present invention is directed to a method and apparatus for providing an interface between a human and a computer. The human end of the interface is preferably a substantially cylindrical object such as a shaft of a surgeon's tool, a catheter, a wire, etc. Alternatively, it can comprise a pool cue, a screw driver shaft, or any other elongated object that is manipulated in 3-dimensional space by a human operator. In certain embodiments of the present invention, the computer develops signals to provide force feedback to the object. For example, a twisting or resisting force can be imparted on the object to provide haptic or force feedback of a medical procedure being performed in a virtual reality simulation.

An apparatus for interfacing with a electrical system includes a support, a gimbal mechanism coupled to the support, and preferably three electromechanical transducers, although certain embodiments (e.g. for use with catheters) may require only two electromechanical transducers. The gimbal mechanism has a base portion which is rotatably coupled to the support to provide a first degree of freedom, and an object receiving portion rotatably coupled to the base portion to provide a second degree of freedom. A first electromechanical transducer is coupled between the support and the base portion, a second electromechanical transducer is coupled between the base portion and the object receiving portion, and a third electromechanical transducer is coupled between the object receiving portion and an intermediate portion of an elongated object that is at least partially disposed within the object receiving portion. The third electromechanical transducer is associated with a third degree of freedom. Therefore, each of the three transducers are associated with a degree of freedom of movement of the object when it is engaged with the object receiving portion of the gimbal mechanism.

More specifically, an apparatus for interfacing an operator manipulable shaft with a computer includes a support, a gimbal mechanism, and four sensors. The gimbal mechanism preferably includes a U shaped base portion having a base and a pair of substantially parallel legs extending therefrom, where the base of the U shaped base portion is rotatably coupled to the support, and a shaft receiving portion pivotally coupled between the legs of the base portion. The shaft receiving portion includes a translation interface and a rotation interface that engage the shaft when it is engaged with an aperture of the shaft receiving portion. The base portion rotates around a first axis and the shaft receiving portion rotates around a second axis substantially perpendicular to the first axis, such that an axis of the shaft defines a radius in a spherical coordinate system having an origin at an intersection of the first axis and the second axis. A first sensor is coupled between the support and the U shaped base portion to provide a first output signal, a second sensor is coupled between the U shaped base portion and the shaft receiving portion to produce a second output signal, a third sensor is coupled to the translation interface to produce a third output signal, and a fourth sensor is coupled between the rotation interface and the object to produce a fourth output signal. The output signals are preferably coupled to an input of a computer by an electronic interface.

In an alternative embodiment of the present invention a first actuator is coupled between the support and the U shaped base portion to produce a movement therebetween in response to a first input electrical signal, a second actuator is coupled between the U shaped base portion and the shaft receiving portion to produce a movement therebetween in response to a second input electrical signal, a third actuator is coupled to the translation interface to produce a mechanical movement of the elongated cylindrical object relative to the shaft receiving portion in response to a third input electrical signal, and a fourth actuator is coupled to the rotation interface to produce a mechanical movement of the elongated cylindrical object relative to the shaft receiving portion in response to a fourth input electrical signal.

A method for providing a human/computer interface includes the steps of: (a) defining an origin in a 3-dimensional space; (b) physically constraining a shaft that can be grasped by an operator such that a portion of the object always intersects the origin and such that the portion of the object extending past the origin defines a radius in a spherical coordinate system; (c) transducing a first electrical signal related to a first angular coordinate of the radius in the spherical coordinate system with a first transducer; (d) transducing a second electrical signal related to a second angular coordinate of the radius in the spherical coordinate system with a second transducer; (e) transducing a third electrical signal related to the length of the radius with a third transducer; and (f) electrically coupling the transducers to a computer system to provide a human/computer interface. The method can further include the step of transducing a fourth electrical signal related to a rotation of the shaft around an axis with a fourth transducer. The transducers are either sensors, actuators, or bidirectional transducers which can serve as either input or sensors.

It will therefore be appreciated that a human/computer interface of the present invention includes a support, a gimbal mechanism coupled to the support, and an elongated shaft engaged with the gimbal mechanism and having a grip area that can be grasped by a hand of an operator. The gimbal mechanism has a base portion rotatably coupled to the support, and a shaft receiving portion rotatably coupled to the base. A first sensor is coupled between the support and the base portion, a second sensor is coupled between the base portion and the shaft receiving portion, and a third sensor is coupled between the shaft receiving portion and an intermediate portion of the shaft. The three sensors are coupled to an input of a computer to provide the human/computer interface. Preferably, the interface further includes a fourth sensor coupled between the shaft receiving portion and an intermediate portion of the shaft, where the third sensor is a translation sensor and the fourth sensor is a rotation sensor.

The advantage of the present invention is that a 3-dimensional human/computer interface tool is provided which has the three or four degrees of freedom available that are desirable for many virtual reality simulation applications. The mechanism of the present invention is relatively straight-forward allowing for low cost production and high reliability. Furthermore, since the human/computer interface tool of the present invention is constrained from movement along at certain degrees of freedom, it can more accurately simulate the use of tools and other elongated mechanical objects which are similarly constrained. Importantly, the present interface is of low inertia since the primary mass of the interface is located at the pivot point. This, along with the light weight of the interface, makes the interface less fatiguing to use.

In another embodiment of the present invention a human/computer interface tool is provided which is provided with only two degrees of freedom. This is particularly advantageous when the shaft is flexible, such as with very thin shafts, wires, catheters, and the like. With, for example, catheters, it is only necessary to provide two degrees of freedom (i.e. in-and-out, and rotation) and, therefore, sensors and/or actuators for the other degrees of freedom do not need to be provided.

These and other advantages of the present invention will become apparent to those skilled in the art upon a reading of the following descriptions of the invention and a study of the several figures of the drawing.

BRIEF DESCRIPTION OF THE DRAWINGS

FIG. 2a is a perspective view of an alternative translation interface used for wires, catheters, and the like;

FIG. 9 is a perspective view of a sensor in accordance with the present invention;

FIG. 9a is a sectional view taken along line 9a—9a of FIG. 9.;

FIG. 9b is a perspective view of an alternative sensing wheel used for wires, catheters, and the like;

DETAILED DESCRIPTION OF THE PREFERRED EMBODIMENTS

Figure 1:
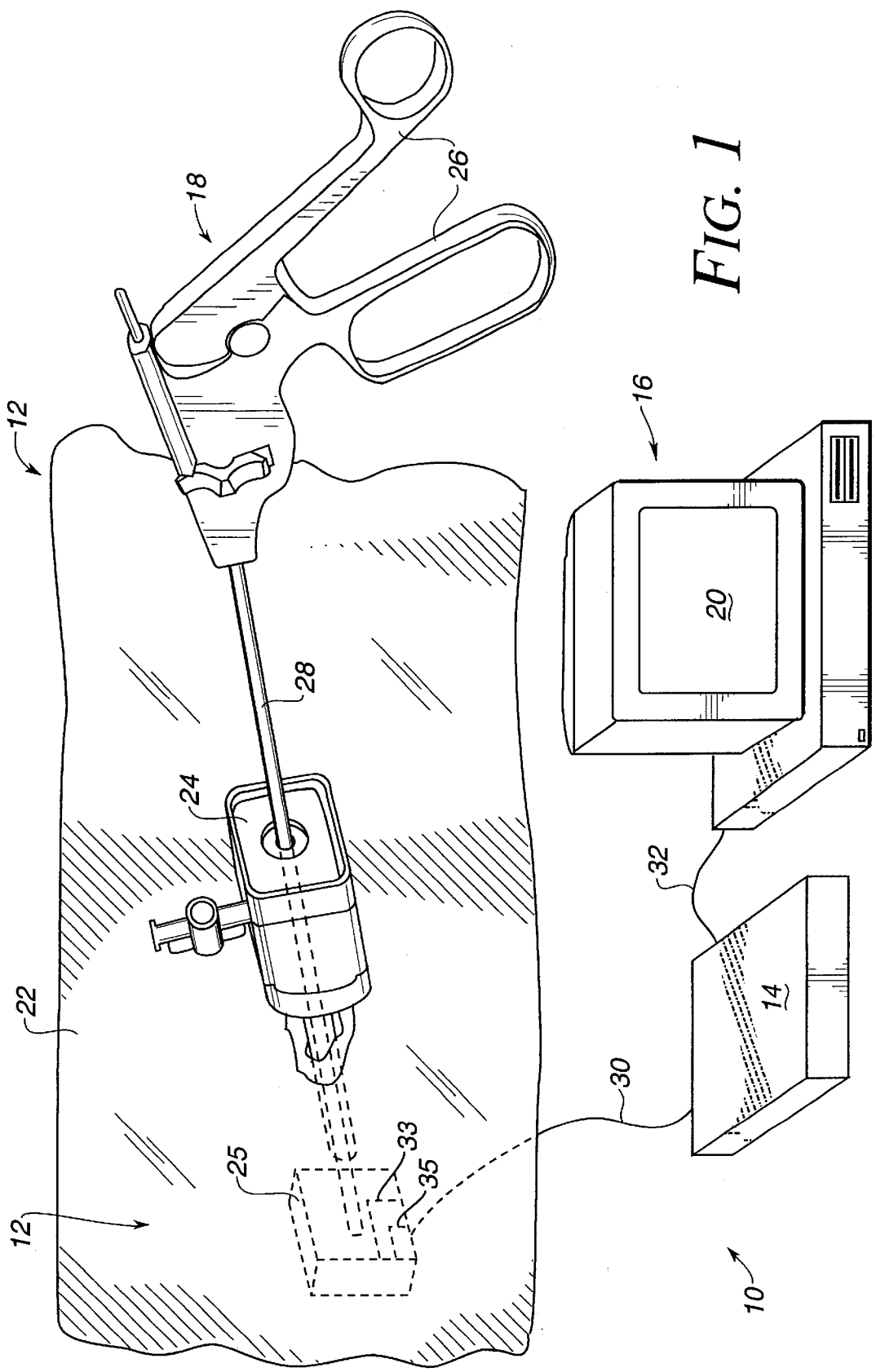
FIG. 1 is a perspective view of a virtual reality system which employs an apparatus of the present invention to interface a laparoscopic tool handle with a computer system.

In FIG. 1, a virtual reality system 10 includes a humani-computer interface apparatus 12, a electronic interface 14, and a computer 16. The illustrated virtual reality system 10 is directed to a virtual reality simulation of a laparoscopic surgery procedure. The software of the simulation is not a part of this invention and thus will not be discussed in. any detail. However, such software is commercially available as, for example, Teleos™ from High Techsplanations of Rockville, Md. Suitable software drivers which interface such simulation software with computer input/output (I/O) devices are available from Immersion Human Interface Corporation of Palo Alto, Calif.

A laparoscopic tool 18 used in conjunction with the present invention is manipulated by an operator and virtual reality images are displayed on a screen 20 of the digital processing system in response to such manipulations. Preferably, the digital processing system is a personal computer or workstation, such as an IBM-PC AT or Macintosh personal computer, or a SUN or Silicon Graphics workstation. Most commonly, the digital processing system is a personal computer which operates under the MS-DOS operating system in conformance with an IBM PC AT standard.

The human/interface apparatus 12 as illustrated herein is used to simulate a laparoscopic medical procedure. In addition to a standard laparoscopic tool 18, the human/interface apparatus 12 includes a barrier 22 and a standard laparoscopic trocar 24. The barrier 22 is used to represent portion of the skin covering the body of a patient. Trocar 24 is inserted into the body of the patient to provide an entry and removal point from the body of the patient for the laparoscopic tool 18, and to allow the manipulation of the laparoscopic tool 18 within the body of the patient while minimizing tissue damage. Laparoscopic tools 18 and trocars 24 are commercially available from sources such as U.S. Surgical of Connecticut. Preferably, the laparoscopic tool 18 is modified such that the end of the tool (such as any cutting edges) are removed, leaving only the handle and the shaft. The end of the laparoscopic tool 18 is not required for the virtual reality simulation, and is removed to prevent any potential damage to persons or property. A gimbal apparatus 25 is shown within the "body" of the patient in phantom lines.

The laparoscopic tool 18 includes a handle or "grip" portion 26 and a shaft portion 28. The shaft portion is an elongated mechanical object and, in particular, is an elongated cylindrical object. The present invention is concerned with tracking the movement of the shaft portion 28 in three-dimensional space, where the movement has been constrained such that the shaft portion 28 has only three or four free degrees of motion. This is a good simulation of the real use of a laparoscopic tool 18 in that once it is inserted into a trocar 24 and through the gimbal apparatus 25, it is limited to about four degrees of freedom. More particularly, the shaft 28 is constrained at some point of along its length such that it can move with four degrees of freedom within the patient's body.

While the present invention will be discussed with reference to the shaft portion 28 of laparoscopic tool 18, it will be appreciated that a great number of other types of objects can be used with the method and apparatus of the present invention. In fact, the present invention can be used with any elongated mechanical object where is desirable to provide a human/computer interface with three or four degrees of freedom. Such objects may include catheters, hypodermic needles, wires, fiber optic bundles, screw drivers, pool cues, etc. Furthermore, although the described preferred embodiment of the present invention contemplates the use of a elongated cylindrical mechanical object, other embodiments of the present invention provide a similar human/computer interface for an elongated mechanical objects which are not cylindrical in shape.

The electronic interface 14 is a part of the human/computer interface apparatus 12 and coupled the apparatus 12 to the computer 16. An electronic interface 14 that is particularly well adopted for the present is described in U.S. patent application Ser. No. 08/092,974, filed Jul. 16, 1993 issued Nov. 19, 1996, as U.S. Pat. No. 5,576,727,and entitled "3-D Mechanical Mouse" assigned to the assignee of the present invention and incorporated herein by reference in its entirety. The electronic interface described therein was designed for the Immersion PROBE™ 3-D mechanical mouse and has six channels corresponding to the six degrees of freedom of the Immersion PROBE. However, in the context of the present invention, the electronic interface 14 requires the use of only four of the six channels, since the present invention is preferably constrained to no more than four degrees of freedom.

The electronic interface 14 is coupled to a gimbal apparatus 25 of the apparatus 12 by a cable 30 and is coupled to the computer 16 by a cable 32. In some embodiments of the present invention, interface 14 serves solely as an input device for the computer 16. In other embodiments of the present invention, interface 14 serves solely as an output device for the computer 16. In yet other embodiments of the present invention, the interface 14 serves as an input/output (I/O) device for the computer 16.

In an alternative embodiment of the present invention, interface 14 has a local microprocessor 33 preferably coupled with any transducers present in the interface 14 and with a transceiver 35. In such an embodiment, the computer 16 is coupled to the transceiver 35 and, typically, not coupled directly with any transducers present in the interface 14. As will be appreciated, the transceiver 35 may be any suitable transceiver capable of bi-directional communication through serial or parallel communication strategies. The local microprocessor 33 will be programmed to execute computer instructions locally such that a computing burden is removed from the computer 16. For example, positional information generated by the transducers may be processed locally by the local microprocessor 33, which in turn can send absolute position and velocity information to the computer 16. Still further, the local microprocessor 33 is capable of receiving incoming force commands from the computer 16, decoding such commands, and controlling the interface 14 accordingly. For more details, see U.S. Pat. No. 5,576,727 of Rosenberg et al.

Figure 2:
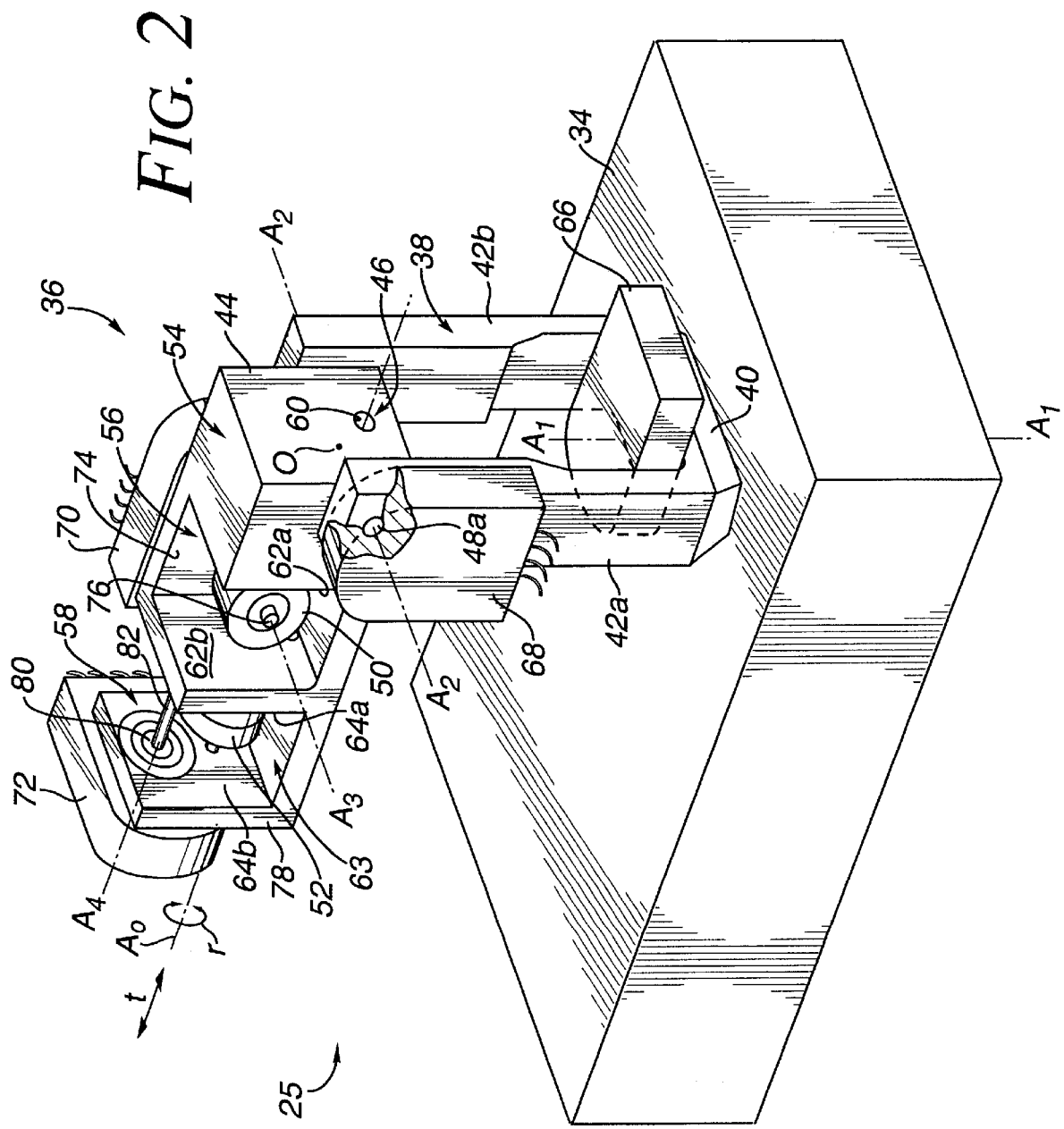
FIG. 2 is a perspective view of an apparatus for mechanically interfacing an elongated mechanical object with an electrical system in accordance with the present invention.

In the perspective view of FIG. 2, the gimbal apparatus 25 of the present invention is illustrated in some detail. The gimbal apparatus 25 includes a support 34 and a gimbal mechanism 36 rotatably coupled to the support. The gimbal mechanism 36 preferably includes a U shaped base portion 38 including a base 40 and a pair of substantially parallel legs 42a and 42b extending upwardly therefrom. As used herein, "substantially parallel" will mean that two objects or axis are exactly or almost parallel, i.e. are at least within five or ten degrees of parallel, and are preferably within less than one degree of parallel. Similarly, the term "substantially perpendicular" will mean that two objects or axis are exactly or almost perpendicular, i.e. at least within five degrees or ten degrees of perpendicular, or more preferably within less than one degree of perpendicular.

The gimbal mechanism 36 also includes an elongated object (shaft) receiving portion 44 provided with an aperture 46 which extends entirely through the object receiving portion. The aperture 46 defines an object axis $A_O$ for an elongated cylindrical object, such that the shaft portion 28 of the laparoscopic tool 18 of FIG. 1. The object receiving portion 44 is at least partially disposed between the legs 42a and 42b of the U shaped base portion, and is pivotally coupled thereto such as by a pair of pivots, one of which is shown as pivot 48a in leg 42a. Another pivot 48b (not shown) is provided in leg 42b.

The object receiving portion 44 also includes a translation interface 50 and a rotation interface 52. The object receiving portion 44 includes a bearing section 54, a translation sensor section 56, and a rotation sensor section 58. The bearing section 54 includes a mass of material provided with a cylindrical bore 60 forming a portion of the aperture 46. The translation sensor section 56 includes a pair of opposing wall surfaces 62a and 62b, each of which is provided with a cylindrical bore receptive to the cylindrical object and forming a part of the aperture 46 which extends through the object receiving portion. The translation sensor section 56 includes a pair of opposing wall surfaces 64a and 64b of a wall 63 and which are provided with cylindrical bores receptive to the cylindrical object and therefore also forming a part of the aperture 46. In consequence, when an elongated cylindrical object is inserted into the object receiving portion 44 along axis $A_O$ it engages the bore 60 of the bearing section 54, and extends through bores provided in the surfaces 62a, 62b, 64a, and 64b to extend completely through the object receiving portion 44 along the aperture 46. In another embodiment of the present invention, wall 63 (and therefore wall surfaces 64a and 64b) is eliminated as being superfluous.

Figure 2A:
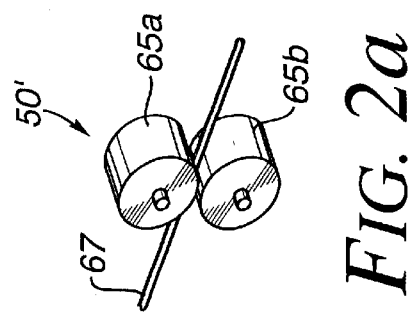

Referring briefly to FIG. 2a, an alternative construction for the translation interface 50 of FIG. 2 is shown at 50'. This alternative translation interface 50' is well adapted for very thin shafts, wires, catheters, and the like. The problem encountered with the translation interface 50 is that, for example, wires and catheters are flexible and therefore do not engage well with a single friction wheel. Therefore, the translation interface 50' includes a drive wheel 65a that is coupled to a sensor and/or actuator, and an idler wheel 65b. The wire or catheter 67 is pinched between the drive wheel 65a and the idler wheel 65b so that there is good frictional engagement between the catheter 67 and the drive wheel 65a.

The object receiving portion 44 is preferably a unitary mass of material made from aluminum or some other lightweight material such as a plastic. The object receiving portion 44 is preferably cast, molded, and/or machined as a monoblock member having the aforementioned bearing section, translation sensory section, and rotation sensory section. The materials and construction of U shaped base portion 38 preferably match the materials and construction techniques used for the production of object receiving portion 44.

The gimbal apparatus 25 illustrated in FIG. 2 constrains an object that is engaged with the object receiving portion 44 to four degrees of freedom. This is accomplished by allowing the U shaped base portion 38 to rotate around an axis $A_1$ relative to the support 34, by allowing the object receiving portion 44 to rotate around an axis $A_2$ relative to the U shaped base portion 38, by allowing the object to translate as illustrated by the arrow t along axis $A_O$ of aperture 46, and by allowing the object to rotate as indicated by arrow r around the axis $A_O$ of aperture 46.

Four electromechanical transducers are used in association with these four degrees of freedom. More particularly, a first degree of freedom electromechanical transducer 66 is arranged to transduce motion and/or force between the U shaped base portion 38 and the support 34, a second degree of freedom electromechanical transducer 68 is arranged to transduce motion and/or force between the U shaped base portion 38 and the object receiving portion 44, a third degree of freedom electromechanical transducer 70 is arranged to transduce motion and/or force between the object receiving portion 44 and an object engaged with the object receiving portion 44, and a fourth degree of freedom transducer 72 is arranged to transduce the motion and/or force between the object receiving portion 44 and an object engaged with the object receiving portion 44.

By "associated with", "related to", or the like, it is meant that the electromechanical transducer is influenced by or influences one of the four degrees of freedom. The electromechanical transducers can be input transducers, in which case they sense motion along a respective degree of freedom and produce an electrical signal corresponding thereto for input into computer 16.

Alternatively, the electromechanical transducers can be output transducers which receive electrical signals from computer 16 that cause the transducers to impart a force on the object in accordance with their respective degrees of freedom. The electromechanical transducers can also be hybrid or bidirectional transducers which operate both as sensors and as actuator devices.

A variety of transducers, readily available in the commercial market are suitable for use in the present invention. For example, if the transducers are input transducers ("sensors"), such sensors can include encoded wheel transducers, potentiometers, etc. Output transducers ("actuators") include stepper motors, servo motors, magnetic particle brakes, friction brakes, pneumatic actuators, etc. Hybrid or bidirectional transducers often pair input and output transducers together, but may also include a purely bidirectional transducer such as a permanent magnet electric motor/generator.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the shaft is placed in a known position within the gimbal mechanism and a calibration signal is provided to the system to provide the reference position mentioned above. All angles provided by the sensors are thereafter relative to that reference position. Such calibration methods are well known to those skilled in the art and, therefore, will not be discussed in any great detail herein.

A preferred input transducer for use of the present invention is an optical encoder model SI marketed by U.S. Digital of Vancouver, Wash. This transducer is an encoded wheel type input transducer. A preferred output transducer for use of the present invention is a d.c. motor model 2434.970-50 produced by Maxon of Fall River, Mass. This type of transducer is a servo motor type output transducer.

There a number of ways of attaching the transducers to the various members of the gimbal apparatus 25. In this preferred embodiment, a housing of transducer 66 is attached to the U shaped base portion 38, and a shaft of the transducer extends through an oversize bore (not shown) in base 40 to engage a press-fit bore (also not shown) in support 34. Therefore, rotation of the U shaped base portion 38 around axis $A_1$ will cause a rotation of a shaft of transducer 66. A housing of transducer 68 is attached to leg 42a of the U shaped base portion 38 such that its shaft forms pivot 48a. Therefore rotation of the object receiving portion 44 around axis $A_2$ will cause a rotation of the shaft of a second transducer 68. The transducer 70 is attached to object receiving portion 44 and extends through a bore (not shown) in a wall 74 of the translation sensor section 56. The shaft 76 provides an axis about which the translation interface 50 can rotate. The fourth transducer 74 is attached to a wall 78 of rotation sensor section 58 and extends through a bore 80 in that wall 78. The shaft 82 of the transducer 72 engages a circumferential surface of rotation interface 52 and rotates therewith.

Axes $A_1$ and $A_2$ are substantially mutually perpendicular and intersect at an origin point O within object receiving portion 44. Axis $A_0$ also intersects this origin O. Shaft 76 rotates around an axis $A_3$ which is substantially perpendicular to the axis $A_0$. Shaft 58 of transducer 72 rotates around an axis $A_4$ which is substantially parallel to the axis $A_0$.

Figure 3:
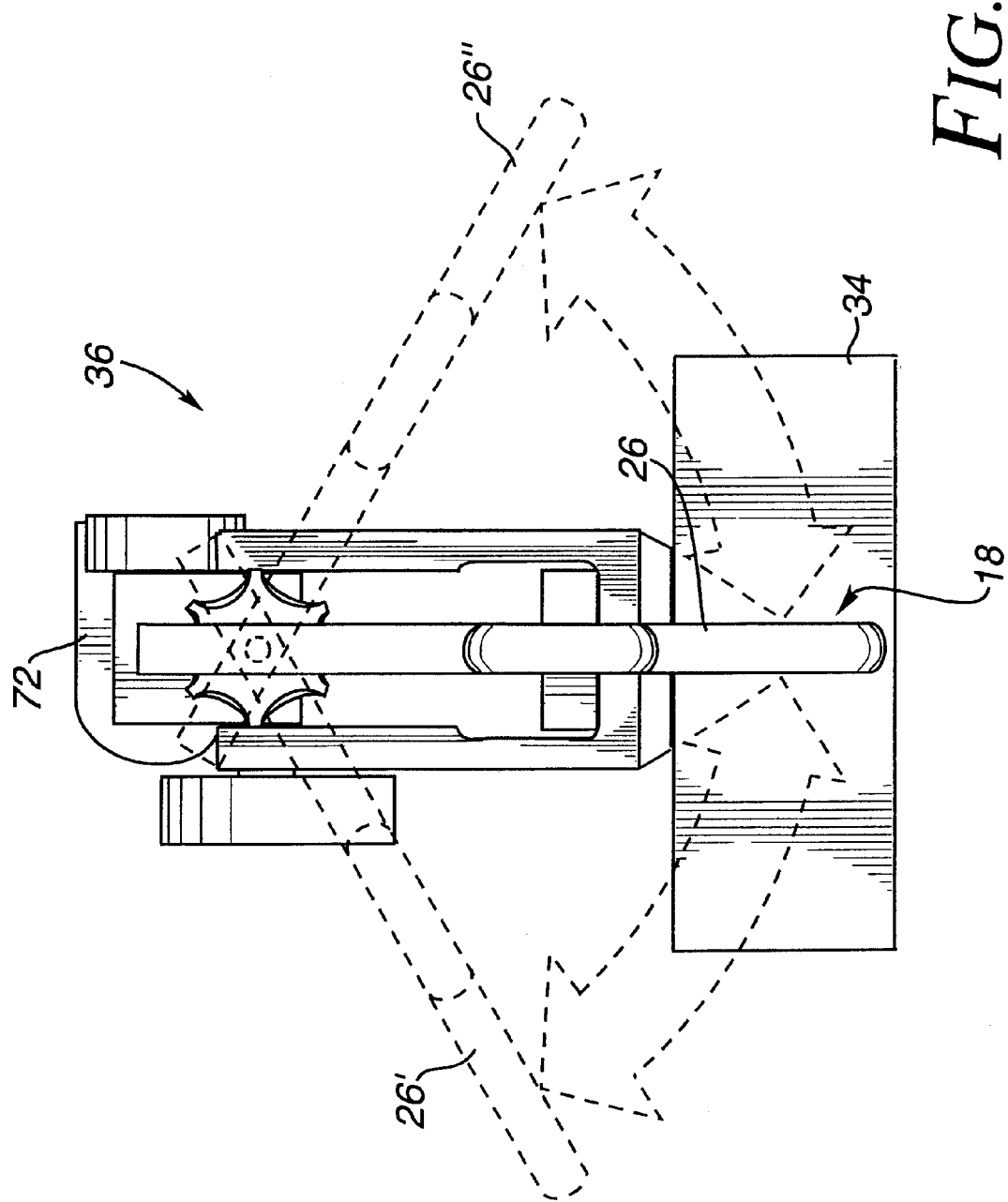
FIG. 3 is front elevation view of the apparatus of FIG. 2 illustrating a laparoscopic tool engaged with an object receiving portion of the present invention.

In FIG. 3, a front view of the gimbal apparatus 25 is used to illustrate one of the degrees of motion of the laparoscopic tool 18. The illustrated degree of freedom is the fourth degree of freedom, i.e. rotation around axis $A_0$ as illustrated by the arrow r in FIG. 2. This degree of freedom is detected by transducer 72. In this fourth degree of motion, the handle portion 26 of the laparoscopic tool 18 can rotate in a clockwise direction as indicated at 26' and in a counter clockwise direction as indicated at 26". Of course, the handle 26 can rotate a full 360° although this would require the release and re-grasping of the handle 26.

Figure 4:
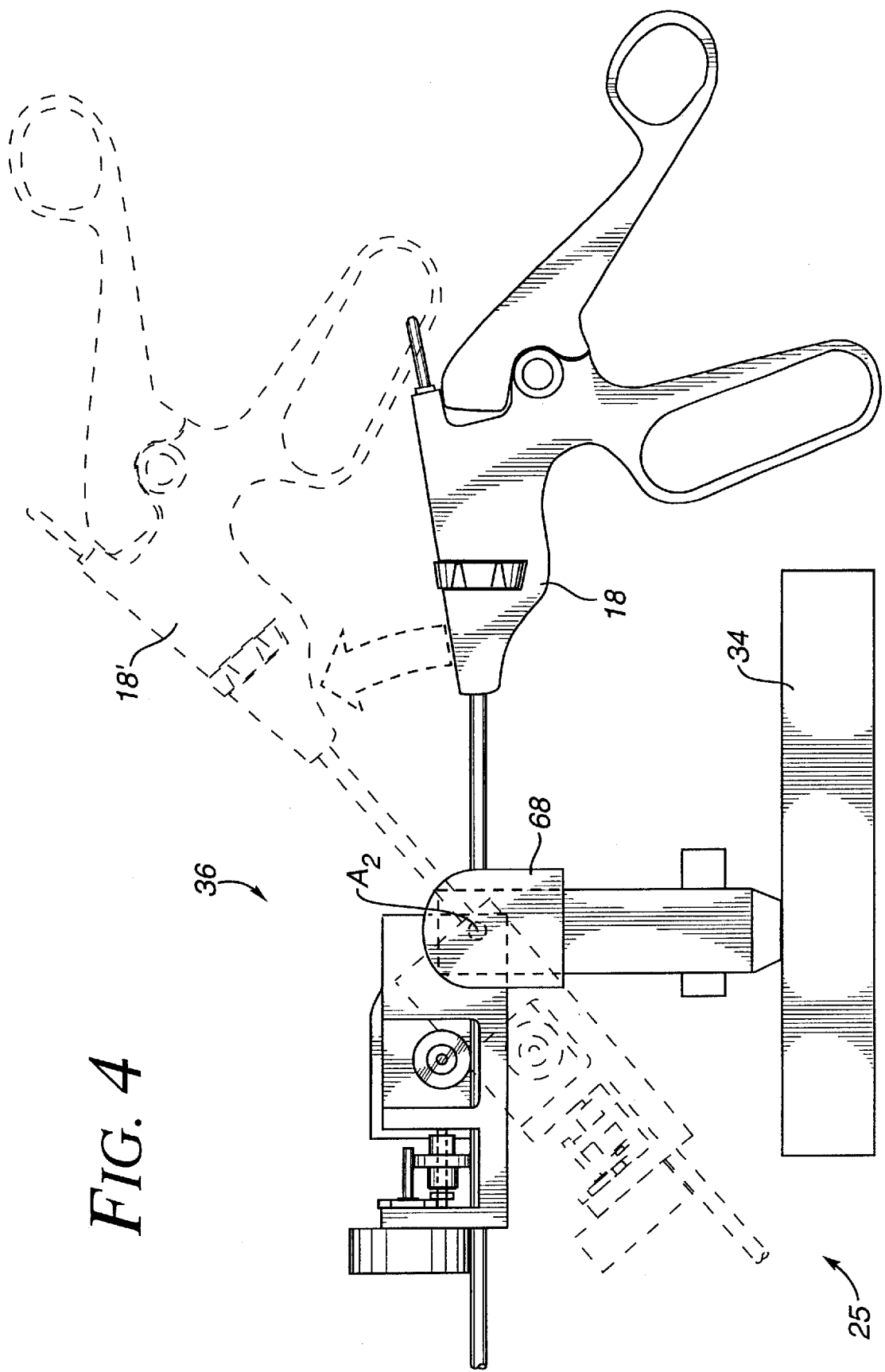
FIG. 4 is a side elevation similarly showing a laparoscopic tool engaged with the object receiving portion of the present invention.

In FIG. 4, a second degree of freedom is illustrated. With this degree of freedom, the laparoscopic tool 18 can pivot upwardly as illustrated at 18' or downwardly (not shown). This rotation around $A_2$ is detected by transducer 68. It should be noted in the present embodiment, the laparoscopic tool 18 cannot rotate 360° around the axis $A_2$ because it is physically constrained by the support 34, portions of the gimbal mechanism 36, etc. However, in the present embodiment, the laparoscopic tool can achieve approximately 170 degrees of rotation around axis $A_2$.

Figure 5:
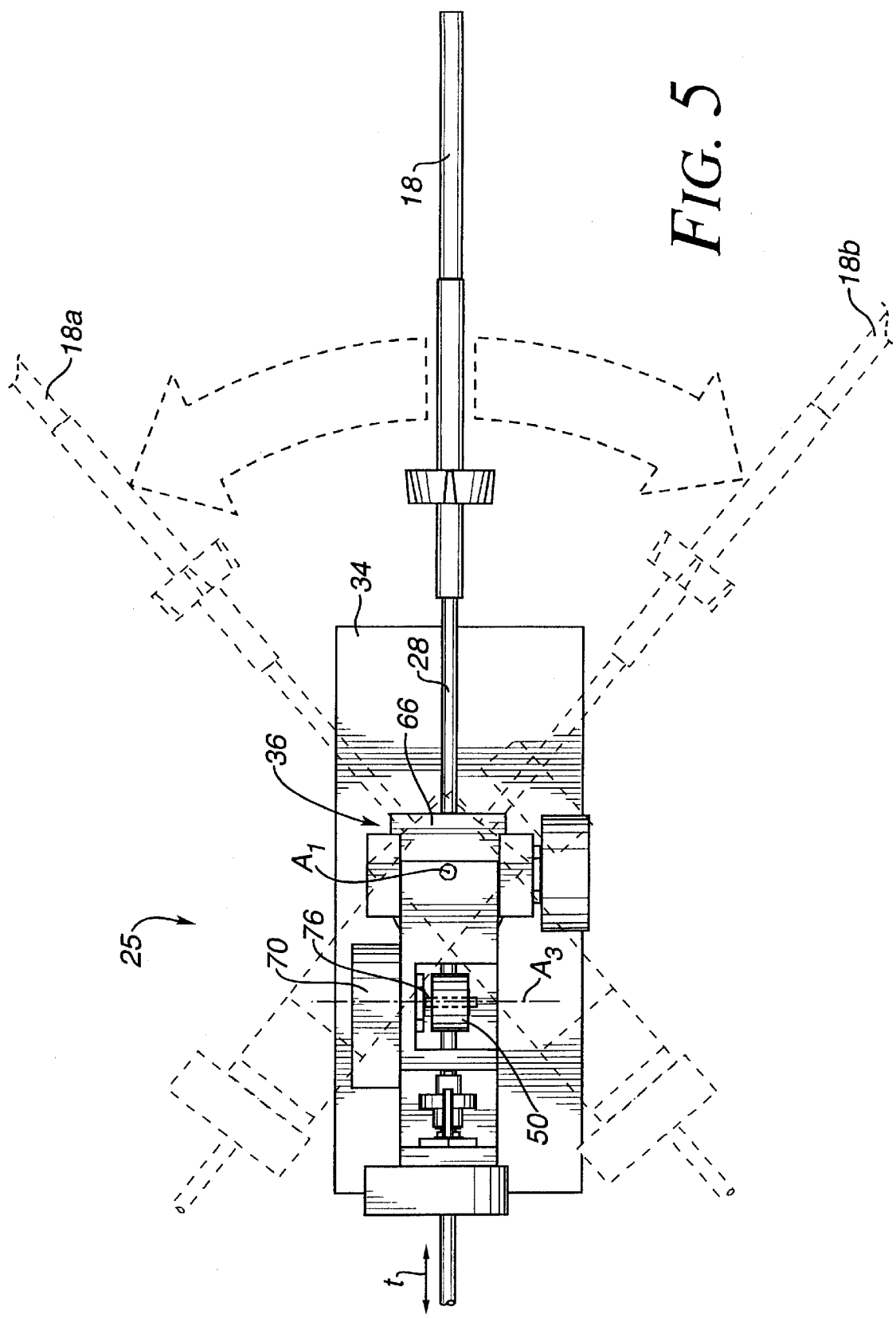
FIG. 5 is a top plan view also illustrating the engagement of a laparoscopic tool with the object receiving portion of the present invention.

FIG. 5 is top view of the gimbal apparatus 25 and illustrates the first and third degrees of freedom. The first degree of freedom is detected by transducer 66 as the laparoscopic tool 18 is pivoted or rotated around axis $A_1$ as illustrated at 18a and 18b. The third degree of freedom is detected by transducer 70 as the shaft portion 28 of laparoscopic tool 18 is moved back and fourth as illustrated by the arrow "t." This causes a rotation of translation interface 50 and the shaft 76 of the third transducer 70.

Figure 6:
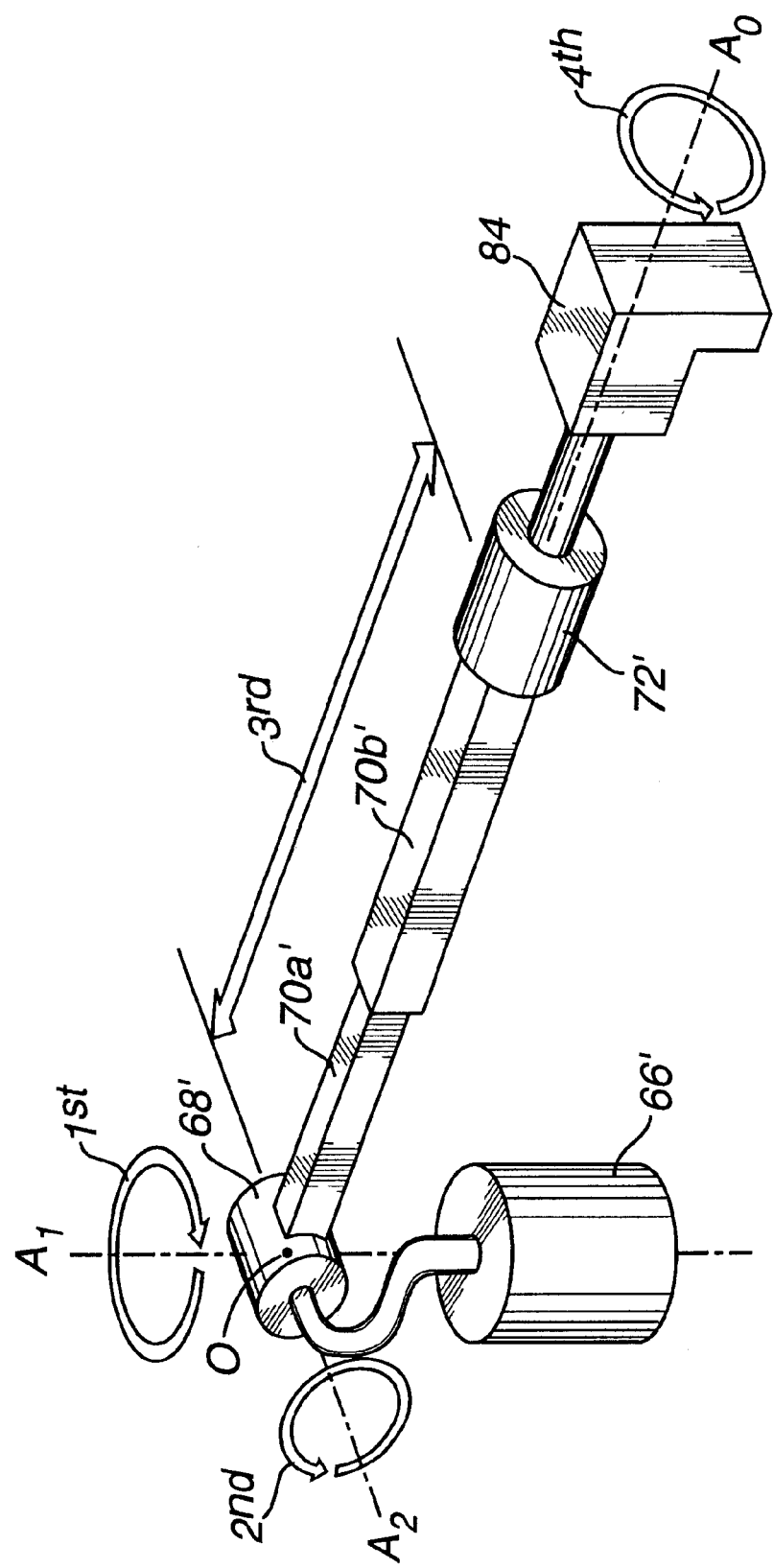
FIG. 6 is a pictorial view illustrating the four degrees of, freedom enjoyed with the mechanism of the present invention.

The four degrees of freedom are illustrated graphically in FIG. 6. The cylinder 66' represents the first transducer 66 and allows a first degree of freedom labeled "1st" around axis $A_1$. Cylinder 68' represents the sensor 68 and allows a second degree of freedom labeled "2nd" around axis $A_2$. Telescoping members 70a' and 70b' represent the third sensor 70 can sense movement along a third degree of freedom labeled "3rd" along axis $A_0$. Finally, a cylinder 72' attached to member 70b' represents the fourth transducer 72 and senses a fourth degree of freedom labeled "4th" around axis $A_0$. A member 84 is provided to indicate position and rotational direction relative to axis $A_0$.

Figure 7:
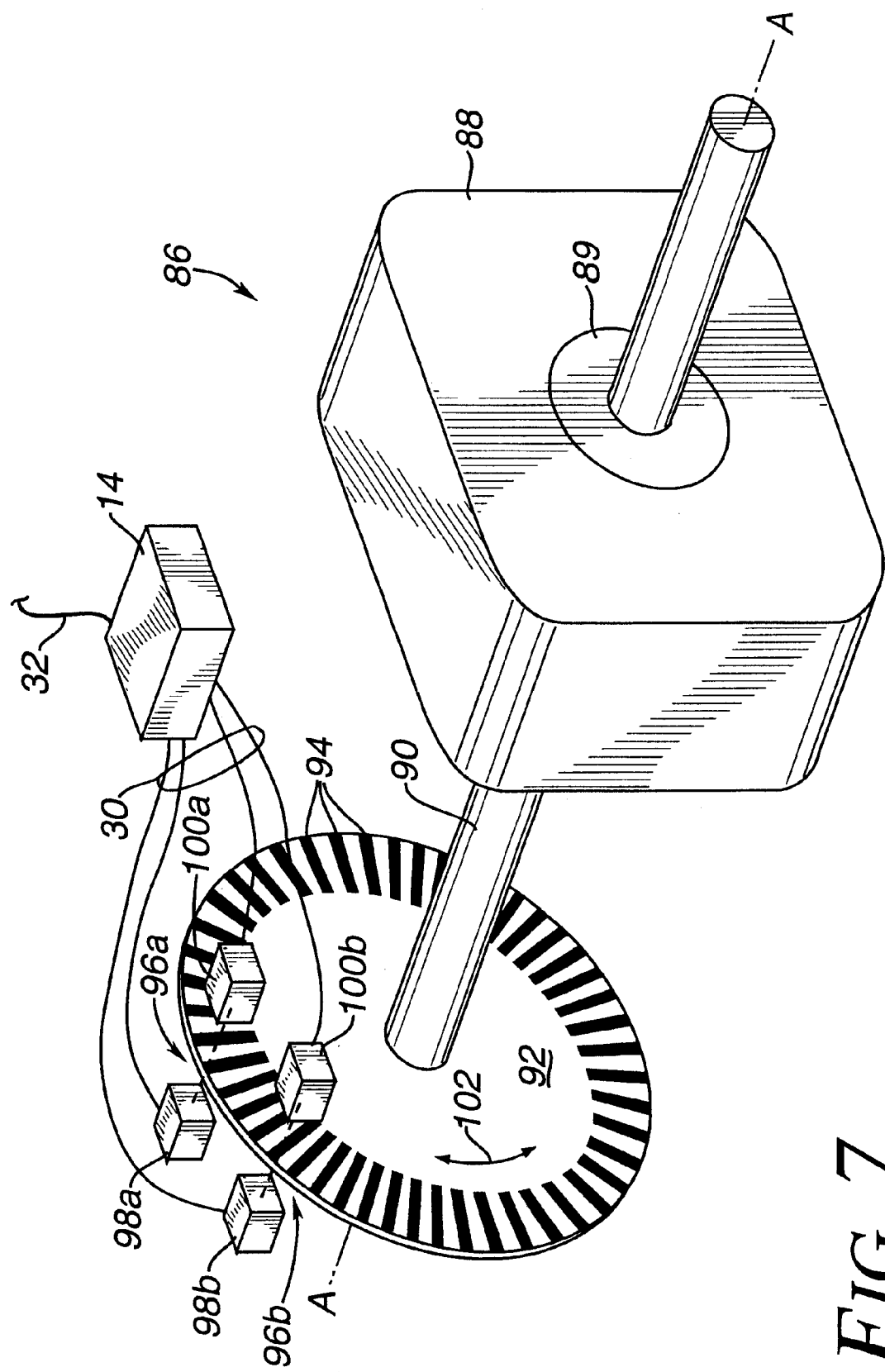
FIG. 7 illustrates a first embodiment of an input sensor.

In FIG. 7, a preferred input transducer (sensor) of the present invention is disclosed. Again, an input transducer of this type can be purchased as sensor model SI from U.S. Digital of Vancouver, Wash. The input transducer 86 includes a bearing block 88 having a bearing 89, a rotary shaft 90 supported by the bearing 89, and a sensing wheel 92 supported for rotation by shaft 90. The sensing wheel is preferably made from a clear, plastic material and is provided with a number of dark radial bands 94 near its circumference, such as by printing or silk screening. A first photodetector pair 96a including a light source 98a and a detector 100a are positioned on opposing sides of the sensing wheel 92 in alignment with the bands 94. Similarly, a second photodetector pair 96b including a light source 98b and a detector 100b are positioned on opposing sides of the sensing wheel 92 in alignment with the bands 94. As the sensing wheel 92 rotates as illustrated at 102 around an axis A, the bands 94 alternatively allow light emanating from light sources 98a and 98b to impinge or not impinge upon the detectors 100a and 100b, respectively. The electronic interface 14, coupled to the photodetector pairs 96a and 96b by cable 30, counts the bands 94 as they pass the photodetector pairs 96a and 96b to provide a signal on cable 32 to the computer 16 indicating the rotational position of the shaft 90 around axis A. The two pairs 96a and 96b are provided to determine the direction of rotation, as is well known to those skilled in the art of sensor design.

Figure 8:
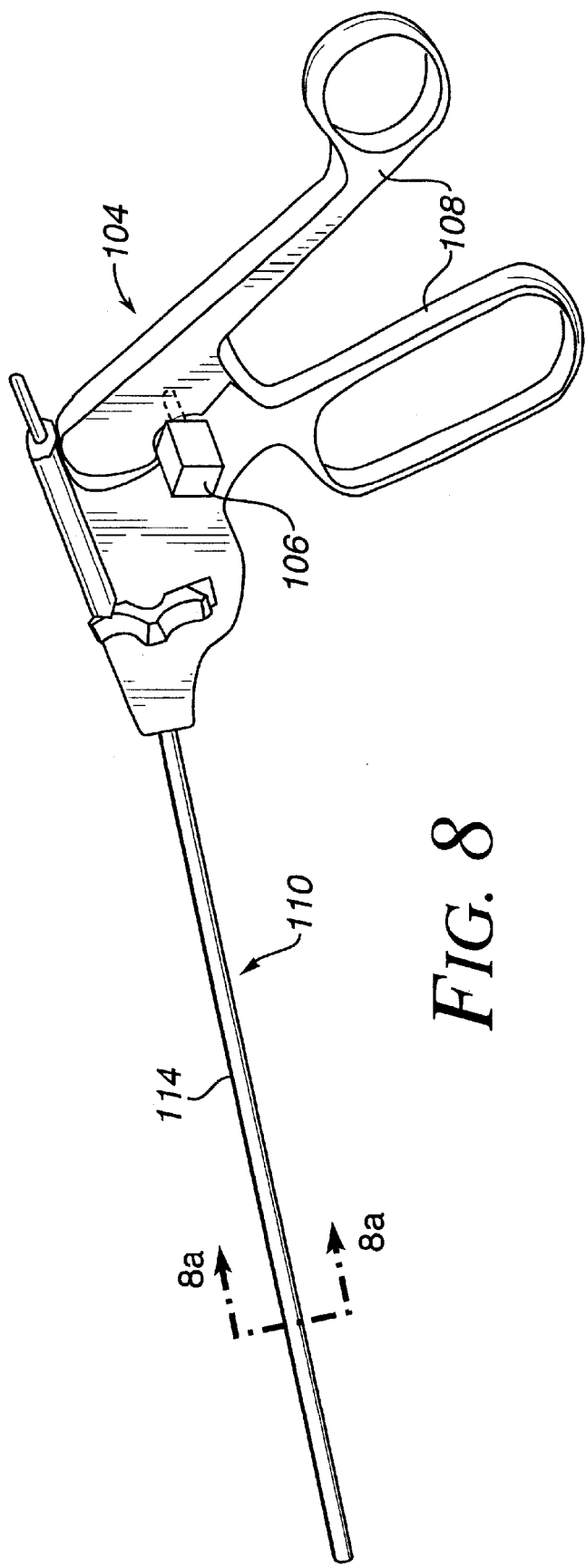
FIG. 8 illustrates a modified laparoscopic tool handle for the use of the present invention.
Figure 8A:
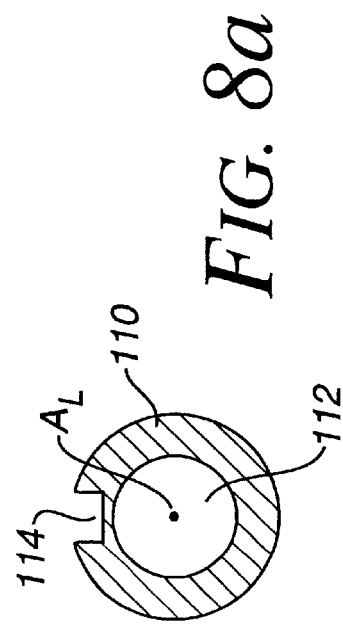
FIG. 8a is a cross-section taken along line 8a—8a of FIG. 8.

FIGS. 8 and 8a illustrate a modified laparoscopic tool 104. More particularly, a sensor 106 has been added to determine when the handle 108 has been squeezed, and the shaft 110 has been grooved or slotted for a purpose to be discussed subsequently. The sensor 106 can be coupled to the computer 16 through electronic interface 14 to provide additional input to the virtual reality system.

With reference to FIG. 8a, the shaft 110 is preferably hollow, having an axial bore 112 which aligns with axis $A_0$, and is provided with an elongated groove 114 which is parallel to an axis $A_L$ of the shaft 110. This elongated groove 114 can be produced by any process including extruding the shaft 110 in the appropriate shape, or cutting the groove 114 with a machine tool, etc.

FIGS. 9 and 9a illustrate an alternate embodiment for transducer 72 which utilizes the shaft 110 and a detector mechanism similar to the one illustrated in FIG. 7. More particularly, the transducer 72' includes a sleeve 115 which is slidingly engaged with shaft 110. As seen in the cross sectional view of FIG. 9a, the sleeve 115 is a substantially cylindrical object having a central bore 116 which engages the circumference 118 of the shaft 110. The sleeve 115 has a key 120 which engages the slot 114 of the shaft 110. Therefore, while the sleeve can slide back and forth along the axis $A_L$ as indicated at 122, but the sleeve 115 rotates with the shaft 110 as indicated at 124 due to the engagement of the key 120 with the groove 114. A sensing wheel 92' is affixed to a circumferential portion of sleeve 115 so that it rotates coaxially with the sleeve 115. A photodetector pair 96' senses the motion of bands 94' and produces an electrical signal on cable 30. The advantage of the embodiment shown in FIGS. 9 and 9a is that rotation of the shaft around axis $A_Z$ is detected without the possibility of slippage. Another advantage of this embodiment is that it is more compact in design.

In FIG. 9b an alternate embodiment for a rotation interface 52' is shown. This alternate embodiment is well adapted for flexible shafts, wires, catheters and the like, such as the aforementioned catheter 67. The rotation interface 52' includes a transducer 72"" that is provided with a resilient grommet 73 having a hole that engages a circumferential portion of the catheter 67. The grommet 73 is preferably a rubber or plastic grommet that causes the catheter 67 to rotate coaxially as the catheter spins or rotates. Preferably, the mass of the transducer 72"" is kept very small so that it only takes a small amount of friction to ensure coaxial rotation of the catheter and transducer without slippage. Because the level of friction is so small, it does not substantially impede translational motion (i.e. in-out motion) of the catheter.

Figure 10A:
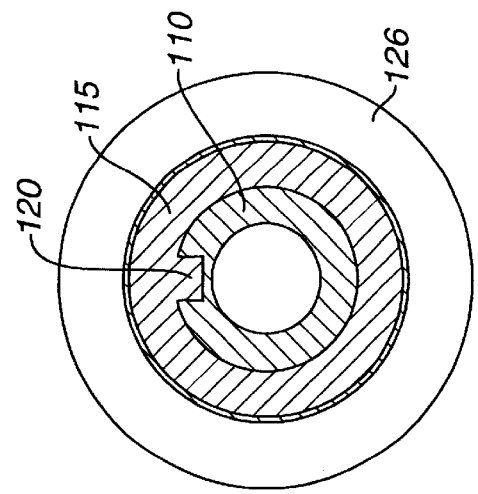
FIG. 10a is a cross sectional view taken along line 10a—10a of FIG. 10.
Figure 10:
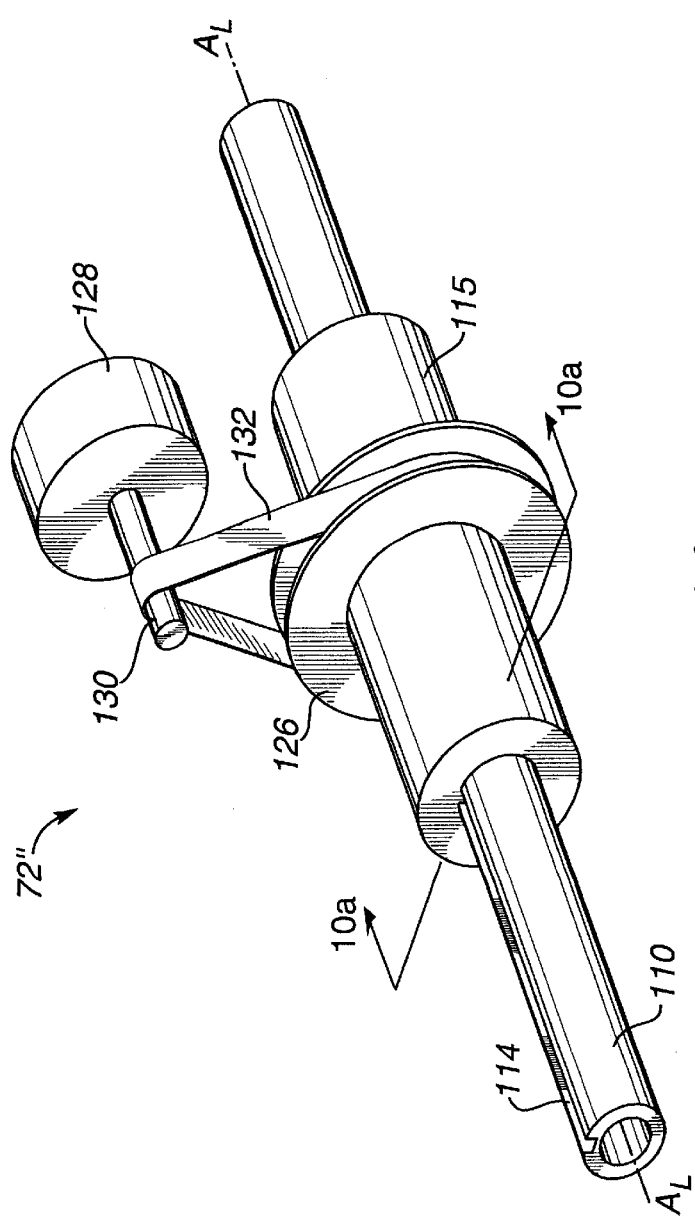
FIG. 10 is a perspective view of and alternative sensor mechanism of the present invention.

FIGS. 10 and 10a illustrate another embodiment 72" for the transducer 72 of FIG. 2. This embodiment has a number of points of similarity with the embodiment discussed with reference to FIGS. 9 and 9a, and it will be appreciated that elements with like reference numerals operate in a similar fashion. However, the embodiment of FIGS. 10 and 10a include a sheave 126 affixed to the circumference of sleeve 115 in the place of the sensing wheel 92' of FIG. 9 and FIG. 9a. A position sensor 128 has a shaft 130 which is coupled to the sheave 126 by a belt 132. The belt 132 can be any continuous loop structure including a resilient, rubber-type belt, a drive-chain type belt, etc. The shaft 130 of position sensor 128 therefore rotates with the sheave 126. The advantage of using a belt 132 or the like is that a substantial amount of force may be applied to the belt to, again, minimize slippage.

Figure 11A:
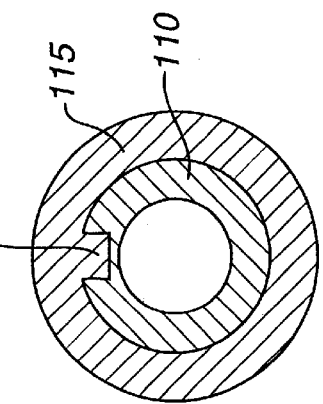
FIG. 11a is a sectional view taken along line 11a—11a of FIG. 11.
Figure 11:
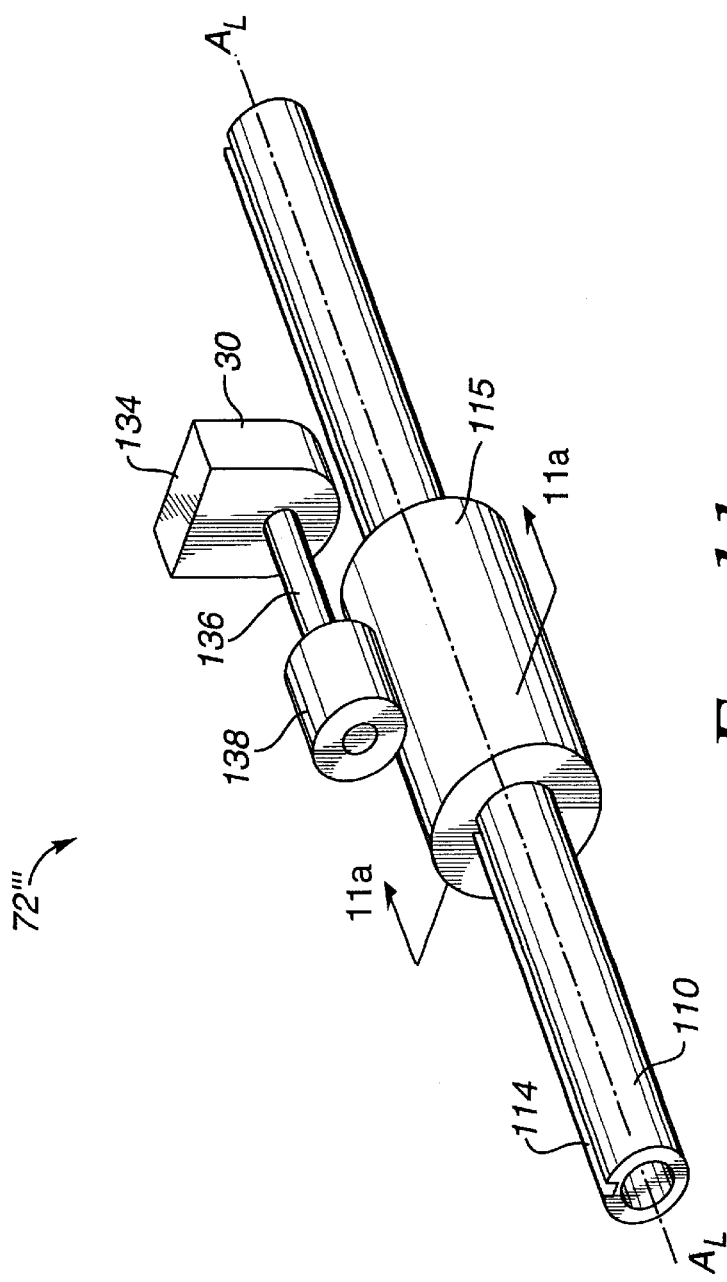
FIG. 11 is a perspective view of another alternative sensor of the present invention.

Another embodiment 72'" for the fourth transducer is illustrated in FIGS. 11 and 11a. Again, there are a number of points of similarity between the embodiments of FIGS. 11 and 11a and the previously described embodiments of FIGS. 9 and 9a and FIGS. 10 and 10a. Therefore, like reference numerals will again refer to like elements. In this embodiment, a sensor 134 has a shaft 136 which serves as the axle of a friction wheel 138 which, in turn, engages a circumferential surface of sleeve 115. Therefore, a rotation of the shaft 110 will cause a rotation of the sleeve 115, which will cause a rotation of the wheel 138 and the shaft 136 to create an electrical signal on cable 30.

With reference to all of the figures, and with particular reference to FIGS. 1 and 2, the shaft 28 of a laparoscopic tool 18 is inserted into aperture 46 along axis $A_O$, causing the shaft 28 to frictionally engage the translation interface (wheel) 50. In this instance, the translational interface 50 is a friction wheel made out of a rubber-like material. The shaft 28 is also in engagement with the rotation interface 52 which, in the embodiment of FIG. 2, is also a friction wheel made out of a rubber-like material. Rotation of the shaft 28 around the axis $A_O$ as illustrated by the arrow r will cause a rotation of the friction wheel 52 and therefore the shaft 82 of the sensor 72. A translation of the shaft 28 along axis $A_O$ will cause a rotation of the friction wheel 50 which rotates the shaft 76 of the transducer 70. A movement up or down of the laparoscopic tool 18 will cause a rotation of the shaft (pivot) 48a of transducer 68, and a side-to-side pivoting of the laparoscopic tool 18 will cause a rotational around axis $A_1$ which is detected by transducer 66.

To this point, the majority of the discussion has been under the assumption that the transducers are input transducers, i.e. the human/computer interface device is used an input device to the computer 16. However, it is also been mentioned that the interface device 12 can serve as an output device for the computer 16. When used as an output device, output transducers ("actuators") are used to respond to electrical signals developed by the computer 16 to impart a force upon the shaft 28 of the laparoscopic tool 18. This can provide useful movement and force (haptic) feedback to the doctor/trainee or other user. For example, if the laparoscopic tool encounters dense mass of tissue or a bone in the "virtual" patient, a force can be generated by transducer 70 making it harder for the doctor/trainee to push the shaft 28 further into the gimbal apparatus 25. Likewise, twisting motions can be imparted on the shaft 28 when the shaft encounters an obstacle within the virtual patient.

It should be noted that force applied to the shaft may not result in any movement of the shaft. This is because the shaft may be inhibited from movement by the hand of the operator who is grasping a handle or grip portion of the shaft. However, the force applied to the shaft may be sensed by the operator as haptic feedback.

With reference to FIG. 2, a method for mechanically interfacing an elongated mechanical object with an electrical system in accordance with the present invention includes first step of defining an origin in 3-dimensional space. This corresponds to the origin O at the intersection of axis $A_1$ and $A_2$. A second step is to physically constrain an elongated object in the 3-dimensional space such that a portion of the object always intersects the origin O and such that a portion of the object extending from the origin O defines a radius in a spherical coordinate system. The elongated object (such as shaft 28 of laparoscopic tool 18) is physically constrained in a 3-dimensional space by the aperture 46 of the object receiving portion 44. The portion of the shaft 28 extending from origin O defines the radius. A third step includes transducing a first electrical signal related to a first angular coordinate of the radius with a first transducer. This corresponds to the operation of transducer 66 which transduces a first electrical signal related to a first angular coordinate of the radius. A fourth step is transducing a second electrical signal related to a second angular coordinate of the radius. This corresponds to the operation of transducer 68 which transduces a second electrical signal. A fifth step is to transduce a third electrical signal related to the length of the radius, which corresponds to the operation of transducer 70. A sixth and final step is to electrically couple the transducers to an electrical system which, in this instance, is preferably a computer 16. An additional, optional step transduces a fourth electrical signal related to a rotation of the object around an object axis which intersects the origin O. This step corresponds to the operation of transducer 72. The transducers can be input transducers, output transducers, or bidirectional transducers.

It will be noted that the electrical system most frequently described in the present invention is a digital processing system or a computer. However, other digital systems, analog systems, and simple electric or electromechanical system can also be utilized with the apparatus and method of the present invention.

It will also be noted that while specific examples of "elongated objects" and "shafts" have been given, that these examples are not meant to be limiting. In general, equivalents of "elongated objects", "elongated cylindrical objects", "shafts", etc. include any object which can be grasped by a human operator to provide an interface between the operator and a computer system. By "grasp", it is meant that operators may releasably engage a grip portion of the object in some fashion, such as by hand, with their fingertips, or even orally in the case of handicapped persons. The "grip" can be a functional grip or handle attached to an elongated portion of the object, or can be a portion of the object itself, such as a portion of the length of a shaft that can be gripped and/or manipulated by the operator.

It should also be noted that flexible shafts, such as wires or catheters, do not always require three or four degrees of freedom. For example, if a human/computer interface for a catheter insertion virtual reality system is desired, only a translation interface (e.g. translation interface 50' of FIG. 2a) and rotation interface (such as rotation interface 52' of FIG. 9c) may be required. This is because a catheter can be moved in and out of a virtual patient (as sensed by translation interface 50') and can be twisted or rotated (as sensed by rotation interface 50'), but cannot be, in any practical manner, moved up or down or from side-to-side due to the flexibility of the catheter. In such applications, therefore, it is desirable to have a human/computer interface with only two degrees of freedom.

While this invention has been described in terms of several preferred embodiments, it is contemplated that alternatives, modifications, permutations and equivalents thereof will become apparent to those skilled in the art upon a reading of the specification and study of the drawings. It is therefore intended that the following appended claims include all such alternatives, modifications, permutations and equivalents as fall within the true spirit and scope of the present invention.

What is claimed is:

1. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user wherein said object receiving portion is moveable in at least two degrees of freedom with respect to a fixed surface;

a transducer coupled to said mechanical apparatus and arranged such that when said elongated mechanical object is at least partially disposed within said object receiving portion, said transducer senses linear displacement of said elongated mechanical object with respect to said object receiving portion and outputs data indicative of said linear displacement; and control electronics coupled to said transducer, said control electronics reporting a representation of said data received from said transducer to said computer system such that said computer system can update a graphical process in response to said data.

2. A control input device as recited in claim 1, wherein said transducer is a first transducer which senses said linear displacement in a first degree of freedom, and further comprising second and third transducers sensing the motion of said object receiving portion in second and third degrees of freedom, respectively, with respect to said fixed surface.

3. A control input device as recited in claim 2, wherein said second and third transducers output second and third data, respectively, indicative of said motion of said object receiving portion in said two degrees of freedom, wherein said control electronics reports a representation of said second and third data from said second and third transducers to said computer system such that said computer system can update a graphical process in response to said second and third data.

4. A control input device as recited in claim 1 wherein said transducer is an optical encoder that engages said elongated mechanical object via a roller in frictional contact with said elongated mechanical object.

5. A control input device as recited in claim 1 wherein said elongated mechanical object is a pool cue.

6. A control input device as recited in claim 5 wherein said pool cue is engaged by a frictional roller when disposed within said object receiving portion.

7. A control input device as recited in claim 6 wherein said frictional roller is coupled to said transducer such that when said pool cue is translated with respect to said object receiving portion, said transducer transduces the relative linear displacement between said pool cue and said object receiving portion.

8. A control input device as recited in claim 7 further comprising a button manipulatable by a user, said control electronics reporting the state of said button to said computer system such that said computer system can update a graphical process in response to said button state.

9. A control input device as recited in claim 7 wherein said transducer is a first transducer, and further comprising second and third transducers that sense motion of said object receiving portion in said two degrees of freedom with respect to said fixed surface.

10. A control input device as recited in claim 9 wherein said control electronics include a local processor coupled to said first, second, and third transducers and providing a representation of data to said computer system.

11. A control input device as recited in claim 7 wherein said graphical process is a simulation of a three dimensional environment.

12. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user;

a transducer coupled to said mechanical apparatus and arranged such that when said elongated mechanical object is at least partially disposed within said object receiving portion, said transducer senses linear displacement of said elongated mechanical object with respect to said object receiving portion and outputs data indicative of said linear displacement;

control electronics coupled to said transducer, said control electronics reporting a representation of said data received from said transducer to said computer system such that said computer system can update a graphical process in response to said data; and a button manipulatable by a user, said control electronics reporting a state of said button to said computer system such that said computer system can update a graphical process in response to said button state.

13. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user;

a transducer coupled to said mechanical apparatus and arranged such that when said elongated mechanical object is at least partially disposed within said object receiving portion, said transducer senses linear displacement of said elongated mechanical object with respect to said object receiving portion and outputs data indicative of said linear displacement; and control electronics coupled to said transducer, said control electronics reporting a representation of said data received from said transducer to said computer system such that said computer system can update a graphical process in response to said data, wherein said control electronics includes a local processor that receives said data and provides said data to said computer system.

14. A control input device as recited in claim 13 wherein said transducer is an optical encoder.

15. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user;

a first transducer coupled to said mechanical apparatus and arranged such that when said elongated mechanical object is at least partially disposed within said object receiving portion, said first transducer senses linear displacement within said mechanical apparatus of said elongated mechanical object with respect to said object receiving portion and outputs data indicative of said linear displacement, and further comprising a second transducer, said second transducer capable of outputting a force on said elongated mechanical object; and control electronics coupled to said first transducer, said control electronics reporting a representation of said data received from said first transducer to said computer system such that said computer system can update a graphical process in response to said data.

16. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user;

a first transducer coupled to said mechanical apparatus and arranged such that when said elongated mechanical object is at least partially disposed within said object receiving portion, said first transducer senses linear displacement of said elongated mechanical object with respect to said object receiving portion and outputs data indicative of said linear displacement, and further comprising a second transducer, said second transducer capable of outputting a force on said elongated mechanical object, wherein said second transducer is a passive brake outputting a frictional resistance force on said elongated mechanical object; and control electronics coupled to said first transducer, said control electronics reporting a representation of said data received from said first transducer to said computer system such that said computer system can update a graphical process in response to said data.

17. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user;

a first transducer coupled to said mechanical apparatus and arranged such that when said elongated mechanical object is at least partially disposed within said object receiving portion, said first transducer senses linear displacement of said elongated mechanical object with respect to said object receiving portion and outputs data indicative of said linear displacement, and further comprising a second transducer, said second transducer capable of outputting a force on said elongated mechanical object, wherein said second transducer is a servo motor outputting a force on said elongated mechanical object; and control electronics coupled to said first transducer, said control electronics reporting a representation of said data received from said first transducer to said computer system such that said computer system can update a graphical process in response to said data.

18. A control input device as recited in claim 15 wherein said user inserts said elongated mechanical object into said object receiving portion to use said control input device.

19. A control input device as recited in claim 15 wherein said control electronics is coupled to said second transducer to control said outputting of said force on said elongated mechanical object.

20. An interface apparatus interfacing the motion of an elongated mechanical object with a computer system, the interface apparatus comprising:

a mechanism including an object receiving portion, said object receiving portion shaped for receiving and engaging said elongated mechanical object physically contacted by and manipulated by a user, wherein said mechanism provides two degrees of freedom to said elongated mechanical object;

a first degree of freedom transducer coupled to said mechanism and arranged such that when said elongated mechanical object is at least partially disposed within said object receiving portion, said transducer senses linear displacement of said elongated mechanical object with respect to said object receiving portion and outputs data indicative of said linear displacement;

a second degree of freedom transducer coupled to said mechanism and arranged to sense pivotal motion of said elongated mechanical object;

an actuator coupled to said mechanism and outputting a force on said elongated mechanical object in said first degree of freedom; and an electronic interface coupled to said first degree of freedom transducer, to said second degree of freedom transducer, and to said actuator, said electronic interface reporting a representation of said data received from said transducers to said computer system such that said computer system can update a graphical process in response to said data, and said electronic interface providing electrical signals from said computer system to said actuator to control said force output by said actuator.

21. An interface apparatus as recited in claim 20 wherein said mechanism includes a base portion rotatably coupled to said object receiving portion, wherein said base portion rotates about a first axis and said object receiving portion rotates around a second axis that is substantially perpendicular to said first axis, and wherein said elongated mechanical object defines a radius in a spherical coordinate system having an origin at an intersection of said first axis and said second axis.

22. An interface apparatus as recited in claim 20 further comprising a third degree of freedom transducer coupled to said mechanism and arranged to sense motion of said elongated mechanical object in a third degree of freedom.

23. An interface apparatus as recited in claim 22 further comprising a fourth degree of freedom transducer coupled to said mechanism and arranged to sense motion of said elongated mechanical object in a third degree of freedom.

24. An interface apparatus as recited in claim 20 wherein said first degree of freedom transducer and said actuator are coupled to a translation wheel having a translation wheel axis that is substantially perpendicular to an object axis along which said object displaces, said translation wheel contacting a surface of said elongated object when said elongated object is engaged with said object receiving portion such that a translation of said elongated object along said object axis causes a rotation of said translation wheel.

25. An interface apparatus as recited in claim 20 wherein said actuator is a first actuator, and further comprising a second actuator coupled to said mechanism and outputting a force on said elongated mechanical object in said second degree of freedom.

26. An interface apparatus as recited in claim 20 wherein said elongated mechanical object is a pool cue.

27. A method for interfacing movements of an elongated mechanical object with a computer system, the method comprising:

receiving and engaging said elongated mechanical object with an object receiving portion of a mechanism, said elongated mechanical object being physically contacted by and manipulated by a user;

sensing linear displacement of said elongated mechanical object in a linear degree of freedom with a sensor with respect to said object receiving portion and outputting data indicative of said linear displacement when said elongated mechanical object is at least partially disposed within said object receiving portion, said data being received by said computer system such that said computer system can update a graphical process in response to said data; and outputting a force on said elongated mechanical object in said linear degree of freedom using an actuator, wherein said force is derived from a signal received from said computer system.

28. A method as recited in claim 27 wherein said sensor is a first sensor, and further comprising sensing rotational movement of said elongated mechanical object in a rotary degree of freedom using a second sensor, and outputting data indicative of said rotational movement to said computer system.

29. A method as recited in claim 28 wherein said actuator is a first actuator, and further comprising outputting a second force on said elongated mechanical object in said rotary degree of freedom using a second actuator, wherein said second force is derived from a second signal received from said computer system.

30. A method as recited in claim 27 wherein said elongated mechanical object is a pool cue.

31. A control input device for interfacing the motion of an elongated mechanical object with a computer system, the control input device comprising:

a mechanical apparatus including an object receiving portion, said object receiving portion shaped to receive and engage said elongated mechanical object held by and manipulated by a user;

a transducer system coupled to said mechanical apparatus and arranged such that when said elongated mechanical object is at least partially disposed within said object receiving portion, said transducer system senses the relative position of said elongated mechanical object with respect to said object receiving portion in at least two degrees of freedom; and control electronics coupled to said transducer system, said control electronics reporting a representation of data received from said transducer system to said computer system such that said computer system can update a graphical process in response to said data.

32. A control input device as recited in claim 31 further comprising a transducer capable of outputting a force on said elongated mechanical object in response to data received from said transducer system in each sensed degree of freedom.

33. A control input device as recited in claim 32 wherein said transducer system comprises a first transducer to sense the relative linear position of said elongated mechanical object and a second transducer to sense the relative rotational position of said elongated mechanical object.

* * * * *